(12) United States Patent
Baek et al.

(10) Patent No.: US 10,909,226 B2
(45) Date of Patent: Feb. 2, 2021

(54) METHOD FOR CONTROLLING BIOSENSOR, AND ELECTRONIC DEVICE

(71) Applicant: SAMSUNG ELECTRONICS CO., LTD., Suwon-si (KR)

(72) Inventors: Seung-Geol Baek, Suwon-si (KR); Kyung-Hoon Song, Yongin-si (KR); Gyu-Sang Cho, Seongnam-si (KR); Yun-Jang Jin, Yongin-si (KR); Kwang-Sub Lee, Yongin-si (KR); Se-Young Jang, Seongnam-si (KR); Heung-Sik Shin, Yongin-si (KR); Chi-Hyun Cho, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/482,334

(22) PCT Filed: Jan. 31, 2018

(86) PCT No.: PCT/KR2018/001356
§ 371 (c)(1),
(2) Date: Jul. 31, 2019

(87) PCT Pub. No.: WO2018/143675
PCT Pub. Date: Aug. 9, 2018

(65) Prior Publication Data
US 2019/0362060 A1  Nov. 28, 2019

(30) Foreign Application Priority Data

Jan. 31, 2017  (KR) .................. 10-2017-0014079

(51) Int. Cl.
*G06F 21/32*  (2013.01)
*A61B 5/00*  (2006.01)
(Continued)

(52) U.S. Cl.
CPC .............. *G06F 21/32* (2013.01); *A61B 5/742* (2013.01); *G06F 3/044* (2013.01); *A61B 5/0022* (2013.01);
(Continued)

(58) Field of Classification Search
None
See application file for complete search history.

(56) References Cited

U.S. PATENT DOCUMENTS 8,570,149 B2 * 10/2013 Rowe ................... A61B 5/1172
340/5.82
9,703,368 B2 * 7/2017 Cho ..................... H04M 1/7253
(Continued)

FOREIGN PATENT DOCUMENTS

KR    10-1296579    8/2013
KR    10-1415644    7/2014
(Continued)

OTHER PUBLICATIONS

International Search Report for PCT/KR2018/001356, dated May 4, 2018, 4 pages.
(Continued)

*Primary Examiner* — K. Wong
(74) *Attorney, Agent, or Firm* — Nixon & Vanderhye, P.C.

(57) ABSTRACT

An electronic device comprising a biosensor is disclosed. The electronic device comprises: the biosensor for acquiring bio-information related to a user; light-emitting circuitry comprising a first light source for outputting light including a designated band; a display panel comprising a second light source for outputting light including one or more pixels; and a processor, wherein the processor can check situation information related to the user, select the corresponding first light source and/or second light source on the basis of the
(Continued)

situation information, and acquire the bio-information through the biosensor by using the selected at least one light source.

15 Claims, 16 Drawing Sheets

(51) Int. Cl.
  *G06F 3/044* (2006.01)
  *A61B 5/01* (2006.01)
  *A61B 5/0205* (2006.01)
  *A61B 5/04* (2006.01)
  *G06F 1/16* (2006.01)
  *G06F 3/0488* (2013.01)

(52) U.S. Cl.
  CPC .............. *A61B 5/01* (2013.01); *A61B 5/0205* (2013.01); *A61B 5/04* (2013.01); *A61B 5/681* (2013.01); *G06F 1/163* (2013.01); *G06F 3/0488* (2013.01)

(56) References Cited

U.S. PATENT DOCUMENTS

| | | | |
|---|---|---|---|
| 9,754,150 B2* | 9/2017 | Wu | G06K 9/0004 |
| 10,037,676 B1* | 7/2018 | Scharf | A61B 5/0013 |
| 10,119,512 B2* | 11/2018 | Kang | F02N 11/0807 |
| 10,410,033 B2* | 9/2019 | He | G06F 3/042 |
| 10,417,473 B2* | 9/2019 | Wu | H01L 27/14649 |
| 10,579,847 B2* | 3/2020 | Cho | G01J 1/0266 |
| 10,627,783 B2* | 4/2020 | Rothkopf | A61B 5/681 |
| 2015/0324566 A1 | 11/2015 | Miura et al. | |
| 2015/0363632 A1 | 12/2015 | Ahn et al. | |
| 2016/0147128 A1 | 5/2016 | Loxley et al. | |

FOREIGN PATENT DOCUMENTS

| | | |
|---|---|---|
| KR | 10-2015-0036665 | 4/2015 |
| KR | 10-2015-0144666 | 12/2015 |
| KR | 10-2016-0099869 | 8/2016 |

OTHER PUBLICATIONS

Written Opinion of the ISA for PCT/KR2018/001356, dated May 4, 2018, 8 pages.

* cited by examiner

METHOD FOR CONTROLLING BIOSENSOR, AND ELECTRONIC DEVICE

CROSS-REFERENCE TO RELATED APPLICATION(S)

This application is a National Phase Entry of PCT International Application No. PCT/KR2018/001356, which was filed on Jan. 31, 2018 and claims a priority under 35 U.S.C. § 119 of the Korean Patent Application No. 10-2017-0014079 filed on Jan. 31, 2017 in Republic of Korea, the disclosures of each of which are incorporated herein by reference in their entireties.

TECHNICAL FIELD

Various embodiments of the present invention relate to biometric sensors interworking with a display and methods of controlling the same.

BACKGROUND ART

An electronic device may include a display and input buttons separate from the display. An input button may include a biometric sensor (e.g., a fingerprint sensor) in part thereof to recognize the user's biometric information (e.g., fingerprint information). At this time, the biometric sensor may be used to detect biometric information about the user's body part. The user may need to perform separate input to the biometric sensor to detect the biometric information or authenticate the user. The size of the display may be limited by the area where the input button takes up the surface where the display of the electronic device is disposed.

The electronic device may perform biometric information authentication on the user using various light sources equipped therein. Each light source in the electronic device may have a different range in performing biometric information authentication on the user, as well as different power consumption. Thus, biometric information authentication may be performed on the user via a proper light source.

DETAILED DESCRIPTION OF THE INVENTION

Technical Problem

A need exists for receiving the user's biometric information according to the user's input (e.g., a fingerprint input to the touchscreen), without any separate physical button from the display and with a biometric sensor placed in part of the display on the front surface of the electronic device. Also needed is identifying whether the user's body part is wet when the user's input is detected by the biometric sensor or whether the user's input is one hacked or spoofed.

The present invention has been conceived to address the foregoing or other problems. According to various embodiments of the present invention, an electronic device and method for controlling the same may obtain the user's context information using fingerprint image analysis or the capacitance of the touch panel, thereby obtaining more reliable biometric information about the user.

Technical Solution

According to various embodiments of the present invention, an electronic device comprises a biometric sensor configured to obtain biometric information related to a user, a light emitting circuit including a first light source configured to output light with a designated band, a display panel including a second light source configured to output light including one or more pixels, and a processor configured to identify context information related to the user, select at least one corresponding light source of the first light source and the second light source based on, at least, the context information, and obtain the biometric information through the biometric sensor using the at least one light source selected.

According to various embodiments of the present invention, there is provided a non-transitory computer-readable recording medium retaining a program executed on a computer, wherein the program comprises executable instructions that, when executed by a processor, enable the processor to identify context information related to a user, select at least one light source of a first light source configured to output light with a designated band and a second light source configured to output light including one or more pixels based on, at least, the context information, and obtain the biometric information through a biometric sensor to obtain biometric information related to the user using the at least one light source selected.

According to various embodiments of the present invention, a method of controlling a biometric sensor may comprise identifying context information related to a user, selecting at least one light source of a first light source configured to output light with a designated band and a second light source configured to output light including one or more pixels based on, at least, the context information, and obtaining the biometric information through a biometric sensor to obtain biometric information related to the user using the at least one light source selected.

Advantageous Effects

According to various embodiments of the present invention, the electronic device may obtain context information related to a user input and use a proper light source equipped in the electronic device based on the obtained information, thereby precisely obtaining the user's biometric information and saving power.

MODE FOR CARRYING OUT THE INVENTION

Figure 1:
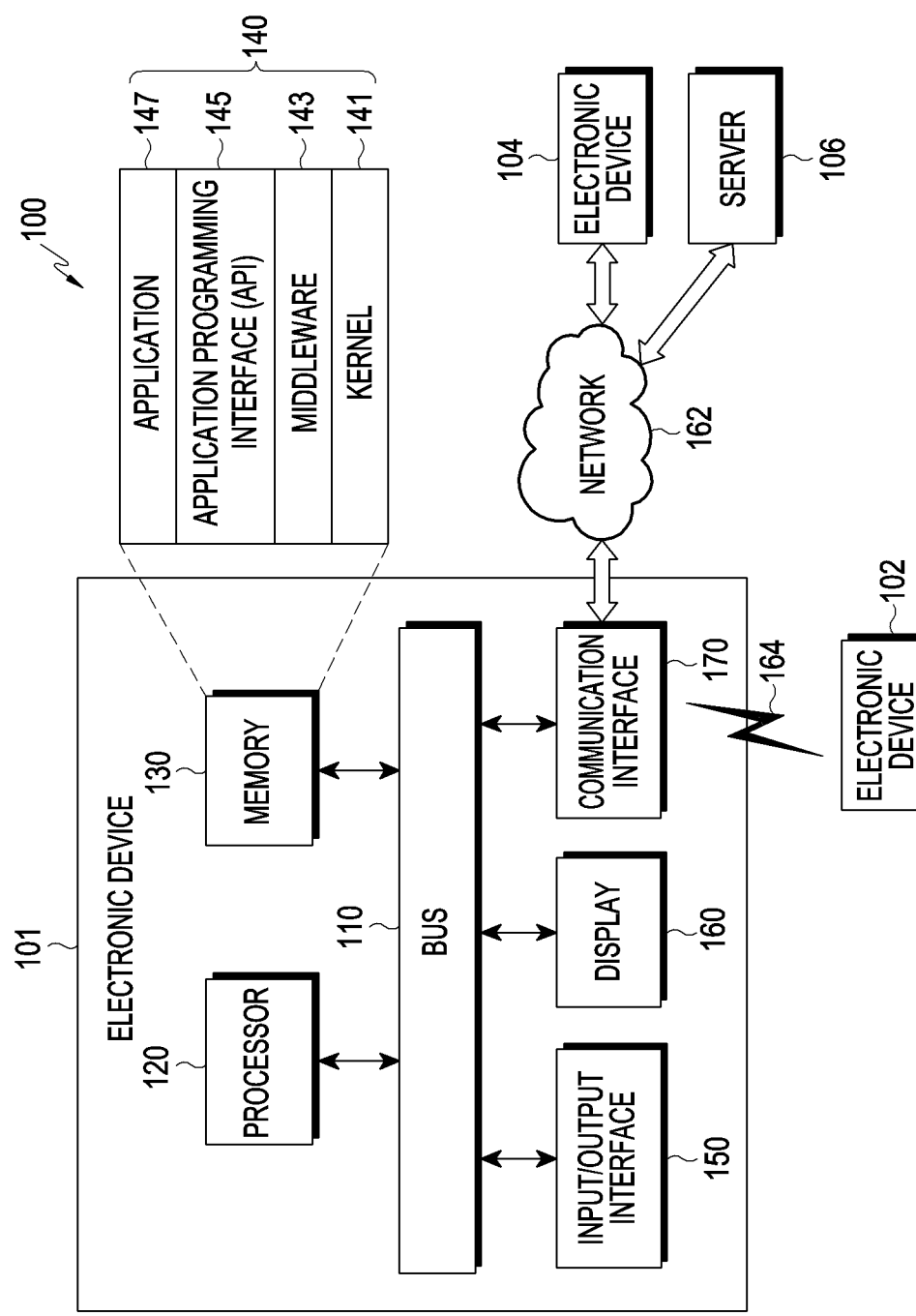
FIG. 1 illustrates a network environment including an electronic device according to various embodiments of the present disclosure.

Hereinafter, embodiments of the present disclosure are described with reference to the accompanying drawings. However, it should be appreciated that the present disclosure is not limited to the embodiments and the terminology used herein, and all changes and/or equivalents or replacements thereto also belong to the scope of the present disclosure. The same or similar reference denotations may be used to refer to the same or similar elements throughout the specification and the drawings. It is to be understood that the singular forms "a," "an," and "the" include plural references unless the context clearly dictates otherwise. As used herein, the terms "A or B" or "at least one of A and/or B" may include all possible combinations of A and B. As used herein, the terms "first" and "second" may modify various components regardless of importance and/or order and are used to distinguish a component from another without limiting the components. It will be understood that when an element (e.g., a first element) is referred to as being (operatively or communicatively) "coupled with/to," or "connected with/to" another element (e.g., a second element), it can be coupled or connected with/to the other element directly or via a third element.

As used herein, the terms "configured to" may be interchangeably used with other terms, such as "suitable for," "capable of," "modified to," "made to," "adapted to," "able to," or "designed to" in hardware or software in the context. Rather, the term "configured to" may mean that a device can perform an operation together with another device or parts. For example, the term "processor configured (or set) to perform A, B, and C" may mean a generic-purpose processor (e.g., a CPU or application processor) that may perform the operations by executing one or more software programs stored in a memory device or a dedicated processor (e.g., an embedded processor) for performing the operations.

For example, examples of the electronic device according to embodiments of the present disclosure may include at least one of a smartphone, a tablet personal computer (PC), a mobile phone, a video phone, an e-book reader, a desktop PC, a laptop computer, a netbook computer, a workstation, a server, a personal digital assistant (PDA), a portable multimedia player (PMP), an MP3 player, a medical device, a camera, or a wearable device. The wearable device may include at least one of an accessory-type device (e.g., a watch, a ring, a bracelet, an anklet, a necklace, glasses, contact lenses, or a head-mounted device (HMD)), a fabric- or clothes-integrated device (e.g., electronic clothes), a body attaching-type device (e.g., a skin pad or tattoo), or a body implantable device. In some embodiments, examples of the smart home appliance may include at least one of a television, a digital video disk (DVD) player, an audio player, a refrigerator, an air conditioner, a cleaner, an oven, a microwave oven, a washer, a drier, an air cleaner, a set-top box, a home automation control panel, a security control panel, a TV box (e.g., Samsung HomeSync™, Apple TV™, or Google TV™), a gaming console (Xbox™, PlayStation™), an electronic dictionary, an electronic key, a camcorder, or an electronic picture frame.

According to an embodiment of the present disclosure, the electronic device may include at least one of various medical devices (e.g., diverse portable medical measuring devices (a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global navigation satellite system (GNSS) receiver, an event data recorder (EDR), a flight data recorder (FDR), an automotive infotainment device, a sailing electronic device (e.g., a sailing navigation device or a gyro compass), avionics, security devices, vehicular head units, industrial or home robots, drones, automatic teller machines (ATMs), point of sale (POS) devices, or Internet of things (IoT) devices (e.g., a bulb, various sensors, a sprinkler, a fire alarm, a thermostat, a street light, a toaster, fitness equipment, a hot water tank, a heater, or a boiler). According to various embodiments of the disclosure, examples of the electronic device may include at least one of part of a piece of furniture, building/structure or vehicle, an electronic board, an electronic signature receiving device, a projector, or various measurement devices (e.g., devices for measuring water, electricity, gas, or electromagnetic waves). According to embodiments of the present invention, the electronic device may be flexible or may be a combination of the above-enumerated electronic devices. According to an embodiment of the disclosure, the electronic devices are not limited to those described above. As used herein, the term "user" may denote a human or another device (e.g., an artificial intelligent electronic device) using the electronic device.

Referring to FIG. 1, according to an embodiment of the present disclosure, an electronic device 100 is included in a network environment 101. The electronic device 101 may include a bus 110, a processor 120, a memory 130, an input/output interface 150, a display 160, and a communication interface 170. In some embodiments, the electronic device 101 may exclude at least one of the components or may add another component. The bus 110 may include a circuit for connecting the components 110 to 170 with one another and transferring communications (e.g., control messages or data) between the components. The processor 120 may include one or more of a central processing unit (CPU), an application processor (AP), or a communication processor (CP). The processor 120 may perform control on at least one of the other components of the electronic device 101, and/or perform an operation or data processing relating to communication.

The memory 130 may include a volatile and/or non-volatile memory. For example, the memory 130 may store commands or data related to at least one other component of the electronic device 101. According to an embodiment of the present disclosure, the memory 130 may store software and/or a program 140. The program 140 may include, e.g., a kernel 141, middlware 143, an application programming interface (API) 145, and/or an application program (or "application") 147. At least a portion of the kernel 141, middleware 143, or API 145 may be denoted an operating system (OS). For example, the kernel 141 may control or manage system resources (e.g., the bus 110, processor 120, or a memory 130) used to perform operations or functions implemented in other programs (e.g., the middleware 143, API 145, or application program 147). The kernel 141 may provide an interface that allows the middleware 143, the API 145, or the application 147 to access the individual components of the electronic device 101 to control or manage the system resources. The memory 130 may include a normal area for storing, e.g., user applications, or a security area for storing information sensitive to security, e.g., information for sensing fingerprints.

The middleware 143 may function as a relay to allow the API 145 or the application 147 to communicate data with the kernel 141, for example. Further, the middleware 143 may process one or more task requests received from the application program 147 in order of priority. For example, the middleware 143 may assign a priority of using system resources (e.g., bus 110, processor 120, or memory 130) of the electronic device 101 to at least one of the application programs 147 and process one or more task requests. The API 145 is an interface allowing the application 147 to control functions provided from the kernel 141 or the middleware 143. For example, the API 133 may include at least one interface or function (e.g., a command) for filing control, window control, image processing or text control. For example, the input/output interface 150 may transfer commands or data input from the user or other external device to other component(s) of the electronic device 101 or may output commands or data received from other component(s) of the electronic device 101 to the user or other external devices.

The display 160 may include, e.g., a liquid crystal display (LCD), a light emitting diode (LED) display, an organic light emitting diode (OLED) display, or a microelectromechanical systems (MEMS) display, or an electronic paper display. The display 160 may display, e.g., various contents (e.g., text, images, videos, icons, or symbols) to the user. The display 160 may include a touchscreen and may receive, e.g., a touch, gesture, proximity or hovering input using an electronic pen or a body portion of the user. For example, the communication interface 170 may set up communication between the electronic device 101 and an external device (e.g., a first electronic device 102, a second electronic device 104, or a server 106). For example, the communication interface 170 may be connected with a network 162 through wireless communication or wired communication and may communicate with an external device (e.g., the second external electronic device 104 or server 106).

The wireless communication may include cellular communication which uses at least one of, e.g., long term evolution (LTE), long term evolution-advanced (LTE-A), code division multiple access (CDMA), wideband code division multiple access (WCDMA), universal mobile telecommunication system (UMTS), wireless broadband (WiBro), or global system for mobile communication (GSM). According to an embodiment of the present invention, the wireless communication may include at least one of, e.g., wireless-fidelity (Wi-Fi), Bluetooth, Bluetooth low power (BLE), Zigbee, near-field communication (NFC), magnetic secure transmission (MST), radio frequency (RF), or body area network (BAN) as denoted with denotation 164 of FIG. 1. According to an embodiment of the present invention, the wireless communication may include global navigation satellite system (GNSS). The GNSS may be, e.g., global positioning system (GPS), global navigation satellite system (Glonass), Beidou navigation satellite system (hereinafter, "Beidou") or Galileo, or the European global satellite-based navigation system. Hereinafter, the terms "GPS" and the "GNSS" may be interchangeably used herein. The wired connection may include at least one of, e.g., universal serial bus (USB), high definition multimedia interface (HDMI), recommended standard (RS)-232, power line communication (PLC), or plain old telephone service (POTS). The network 162 may include at least one of telecommunication networks, e.g., a computer network (e.g., local area network (LAN) or wide area network (WAN)), Internet, or a telephone network.

The first and second external electronic devices 102 and 104 each may be a device of the same or a different type from the electronic device 101. According to an embodiment of the present disclosure, all or some of operations executed on the electronic device 101 may be executed on another or multiple other electronic devices (e.g., the electronic devices 102 and 104 or server 106). According to an embodiment of the present disclosure, when the electronic device 101 should perform some function or service automatically or at a request, the electronic device 101, instead of executing the function or service on its own or additionally, may request another device (e.g., electronic devices 102 and 104 or server 106) to perform at least some functions associated therewith. The other electronic device (e.g., electronic devices 102 and 104 or server 106) may execute the requested functions or additional functions and transfer a result of the execution to the electronic device 101. The electronic device 101 may provide a requested function or service by processing the received result as it is or additionally. To that end, a cloud computing, distributed computing, or client-server computing technology may be used, for example.

According to various embodiments of the present invention, an electronic device comprises a biometric sensor configured to obtain biometric information related to a user, a light emitting circuit including a first light source configured to output light with a designated band, a display panel including a second light source configured to output light including one or more pixels, and a processor configured to identify context information related to the user, select at least one corresponding light source of the first light source and the second light source based on, at least, the context information, and obtain the biometric information through the biometric sensor using the at least one light source selected.

In the electronic device according to various embodiments of the present invention, the context information may include information about whether the first light source is additionally needed to obtain the biometric information based on the state of the image obtained using the biometric sensor.

In the electronic device according to various embodiments of the present invention, upon determining that the first light source is additionally needed, the processor may be configured to obtain additional biometric information through the biometric sensor using the first light source.

In an electronic device according to various embodiments of the present invention, a touch panel may be included which is disposed on the display panel. The context information may include the capacitance of the touch panel according to the user's input detected to obtain the user's biometric information. When the capacitance of the touch panel where the user's input is detected is higher than a preset threshold, the processor may obtain the biometric information through the biometric sensor using the first light source.

According to various embodiments of the present invention, the processor may identify the capacitance of at least one point of the touch where the user's input is detected and compare the capacitance of the at least one point with the preset threshold.

According to various embodiments of the present invention, the processor may be configured to generate a third image by combining a first image obtained using the first light source and a second image obtained using the second light source and obtain the biometric information using the generated third image.

According to various embodiments of the present invention, the context information may include a security level corresponding to the electronic device. The processor may be configured to obtain the biometric information based on the first light source when the security level is higher than a predesignated security level.

According to various embodiments of the present invention, the processor may be configured to perform spoofing filtering using at least one of capacitances of the first light source and the touch panel and identify the context information according to a result of the spoofing filtering.

Figure 2:
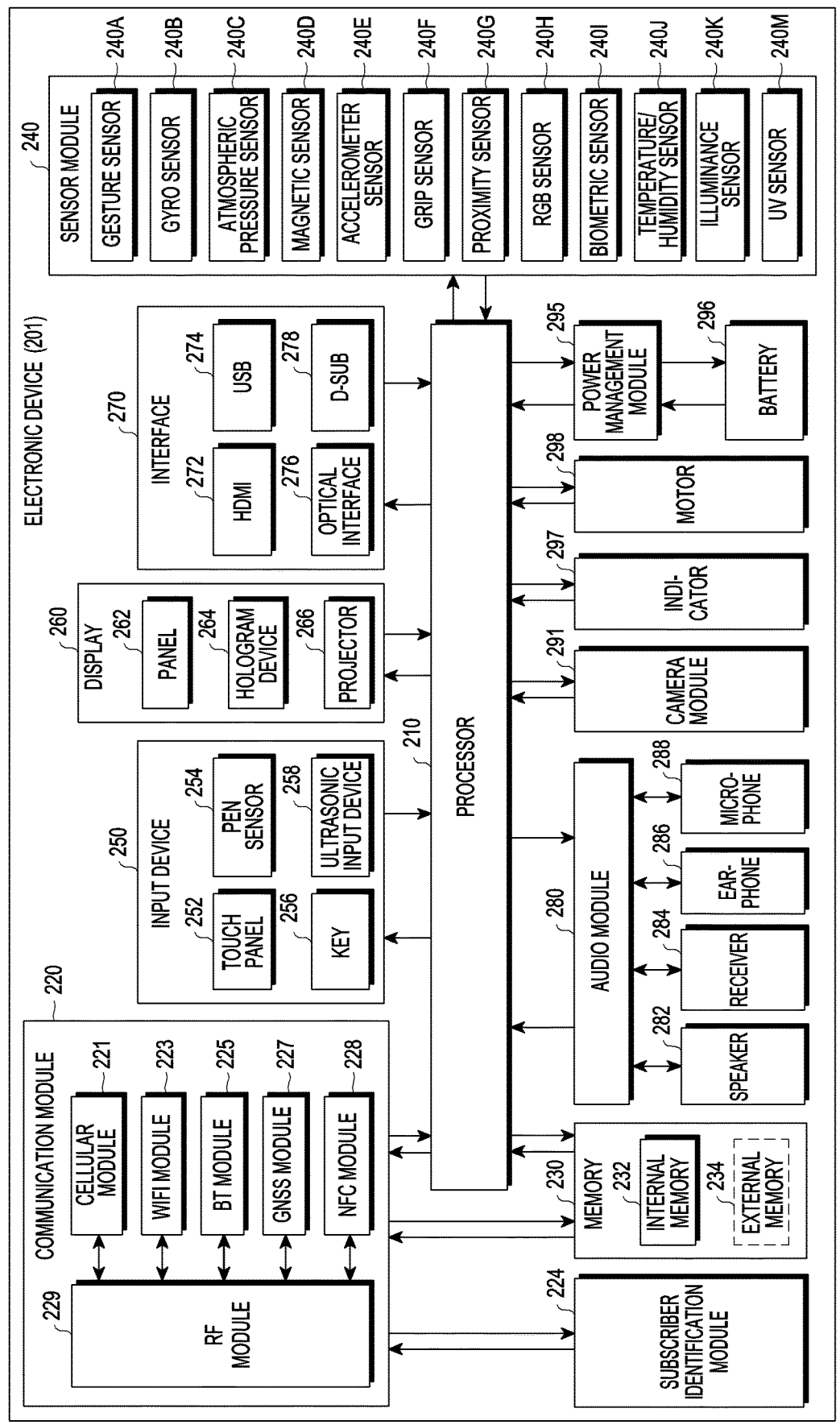
FIG. 2 is a block diagram illustrating an electronic device according to various embodiments of the present invention.

FIG. 2 is a block diagram illustrating an electronic device 201 according to various embodiments. The electronic device 201 may include the whole or part of the configuration of, e.g., the electronic device 101 shown in FIG. 1. The electronic device 201 may include one or more processors (e.g., application processors (APs)) 210, a communication module 220, a subscriber identification module (SIM) 224, a memory 230, a sensor module 240, an input device 250, a display 260, an interface 270, an audio module 280, a camera module 291, a power management module 295, a battery 296, an indicator 297, and a motor 298. The processor 210 may control multiple hardware and software components connected to the processor 210 by running, e.g., an operating system or application programs, and the processor 210 may process and compute various data. The processor 210 may be implemented in, e.g., a system on chip (SoC). According to an embodiment, the processor 210 may further include a graphic processing unit (GPU) and/or an image signal processor. The processor 210 may include at least some (e.g., the cellular module 221) of the components shown in FIG. 2. The processor 210 may load a command or data received from at least one of other components (e.g., a non-volatile memory) on a volatile memory, process the command or data, and store resultant data in the non-volatile memory.

The communication module 220 may have the same or similar configuration to the communication interface 170.

The communication module 220 may include, e.g., a cellular module 221, a wireless fidelity (Wi-Fi) module 223, a Bluetooth (BT) module 225, a GNSS module 227, a NFC module 228, and a RF module 229. The cellular module 221 may provide voice call, video call, text, or Internet services through, e.g., a communication network. The cellular module 221 may perform identification or authentication on the electronic device 201 in the communication network using a subscriber identification module 224 (e.g., the SIM card). According to an embodiment, the cellular module 221 may perform at least some of the functions providable by the processor 210. According to an embodiment, the cellular module 221 may include a communication processor (CP). According to an embodiment of the present invention, at least some (e.g., two or more) of the cellular module 221, the Wi-Fi module 223, the Bluetooth module 225, the GNSS module 227, or the NFC module 228 may be included in a single integrated circuit (IC) or an IC package. The RF module 229 may communicate data, e.g., communication signals (e.g., RF signals). The RF module 229 may include, e.g., a transceiver, a power amplifier module (PAM), a frequency filter, a low noise amplifier (LNA), or an antenna. According to various embodiments, at least one of the cellular module 221, the Wi-Fi module 223, the Bluetooth module 225, the GNSS module 227, or the NFC module 228 may communicate RF signals through a separate RF module. The subscription identification module 224 may include, e.g., a card including a subscriber identification module, or an embedded SIM, and may contain unique identification information (e.g., an integrated circuit card identifier (IC-CID) or subscriber information (e.g., an international mobile subscriber identity (IMSI)).

The memory 230 (e.g., the memory 130) may include, e.g., an internal memory 232 or an external memory 234. The internal memory 232 may include at least one of, e.g., a volatile memory (e.g., a dynamic RAM (DRAM), a static RAM (SRAM), a synchronous dynamic RAM (SDRAM), etc.) or a non-volatile memory (e.g., a one-time programmable ROM (OTPROM), a programmable ROM (PROM), an erasable and programmable ROM (EPROM), an electrically erasable and programmable ROM (EEPROM), a mask ROM, a flash ROM, a flash memory (e.g., a NAND flash, or a NOR flash), a hard drive, or solid state drive (SSD). The external memory 234 may include a flash drive, e.g., a compact flash (CF) memory, a secure digital (SD) memory, a micro-SD memory, a min-SD memory, an extreme digital (xD) memory, a multi-media card (MMC), or a Memory Stick™. The external memory 234 may be functionally or physically connected with the electronic device 201 via various interfaces.

For example, the sensor module 240 may measure a physical quantity or detect an operational state of the electronic device 201, and the sensor module 240 may convert the measured or detected information into an electrical signal. The sensor module 240 may include at least one of, e.g., a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., a red-green-blue (RGB) sensor, a bio sensor 240I, a temperature/humidity sensor 240J, an illumination sensor 240K, or an Ultra Violet (UV) sensor 240M. Additionally or alternatively, the sensing module 240 may include, e.g., an e-nose sensor, an electromyography (EMG) sensor, an electroencephalogram (EEG) sensor, an electrocardiogram (ECG) sensor, an infrared (IR) sensor, an iris sensor, or a finger print sensor. The sensor module 240 may further include a control circuit for controlling at least one or more of the sensors included in the sensing module. According to an embodiment, the electronic device 201 may further include a processor configured to control the sensor module 240 as part of the processor 210 or separately from the processor 210 and the electronic device 2701 may control the sensor module 240 while the processor 210 is in a sleep mode.

The input unit 250 may include, e.g., a touch panel 252, a (digital) pen sensor 254, a key 256, or an ultrasonic input device 258. The touch panel 252 may use at least one of capacitive, resistive, infrared, or ultrasonic methods. The touch panel 252 may further include a control circuit. The touch panel 252 may further include a tactile layer and may provide a user with a tactile reaction. The (digital) pen sensor 254 may include, e.g., a part of a touch panel or a separate sheet for recognition. The key 256 may include e.g., a physical button, optical key or keypad. The ultrasonic input device 258 may sense an ultrasonic wave generated from an input tool through a microphone (e.g., the microphone 288) to identify data corresponding to the sensed ultrasonic wave.

The display 260 (e.g., the display 160) may include a panel 262 (or a display panel), a hologram device 264, a projector 266, and/or a control circuit for controlling the same. The panel 262 may be implemented to be flexible, transparent, or wearable. The panel 262, together with the touch panel 252, may be configured in one or more modules. According to an embodiment of the present invention, the panel 262 may include a pressure sensor (or pose sensor) that may measure the strength of a pressure by the user's touch. The pressure sensor may be implemented in a single body with the touch panel 252 or may be implemented in one or more sensors separate from the touch panel 252. The hologram device 264 may make three dimensional (3D) images (holograms) in the air by using light interference. The projector 266 may display an image by projecting light onto a screen. The screen may be, for example, located inside or outside of the electronic device 201. The interface 270 may include e.g., a high definition multimedia interface (HDMI) 272, a USB 274, an optical interface 276, or a D-subminiature (D-sub) 278. The interface 270 may be included in e.g., the communication interface 170 shown in FIG. 1. Additionally or alternatively, the interface 270 may include a mobile high-definition link (MHL) interface, a secure digital (SD) card/multimedia card (MMC) interface, or infrared data association (IrDA) standard interface.

The audio module 280 may convert, e.g., a sound signal into an electrical signal and vice versa. At least a part of the audio module 280 may be included in, e.g., the input/output interface 145 as shown in FIG. 1. The audio module 280 may process sound information input or output through, e.g., a speaker 282, a receiver 284, an earphone 286, or a microphone 288. For example, the camera module 291 may be a device for capturing still images and videos, and may include, according to an embodiment of the present disclosure, one or more image sensors (e.g., front and back sensors), a lens, an image signal processor (ISP), or a flash such as an LED or xenon lamp. The power manager module 295 may manage power of the electronic device 201, for example. According to an embodiment of the present invention, the power manager module 295 may include a power management Integrated circuit (PMIC), a charger IC, or a battery or fuel gauge. The PMIC may have a wired and/or wireless recharging scheme. The wireless charging scheme may include e.g., a magnetic resonance scheme, a magnetic induction scheme, or an electromagnetic wave based scheme, and an additional circuit, such as a coil loop, a resonance circuit, a rectifier, or the like may be added for wireless charging. The battery gauge may measure an amount of remaining power of the battery 296, a voltage, a current, or a temperature while the battery 296 is being charged. The battery 296 may include, e.g., a rechargeable battery or a solar battery.

The indicator 297 may indicate a particular state of the electronic device 201 or a part (e.g., the processor 210) of the electronic device, including e.g., a booting state, a message state, or recharging state. The motor 298 may convert an electric signal to a mechanical vibration and may generate a vibrational or haptic effect. The electronic device 201 may include a mobile TV supporting device (e.g., a GPU) that may process media data as per, e.g., digital multimedia broadcasting (DMB), digital video broadcasting (DVB), or MediaFlo' standards. Each of the aforementioned components of the electronic device may include one or more parts, and a name of the part may vary with a type of the electronic device. According to various embodiments, the electronic device (e.g., the electronic device 201) may exclude some elements or include more elements, or some of the elements may be combined into a single entity that may perform the same function as by the elements before combined.

Figure 3:
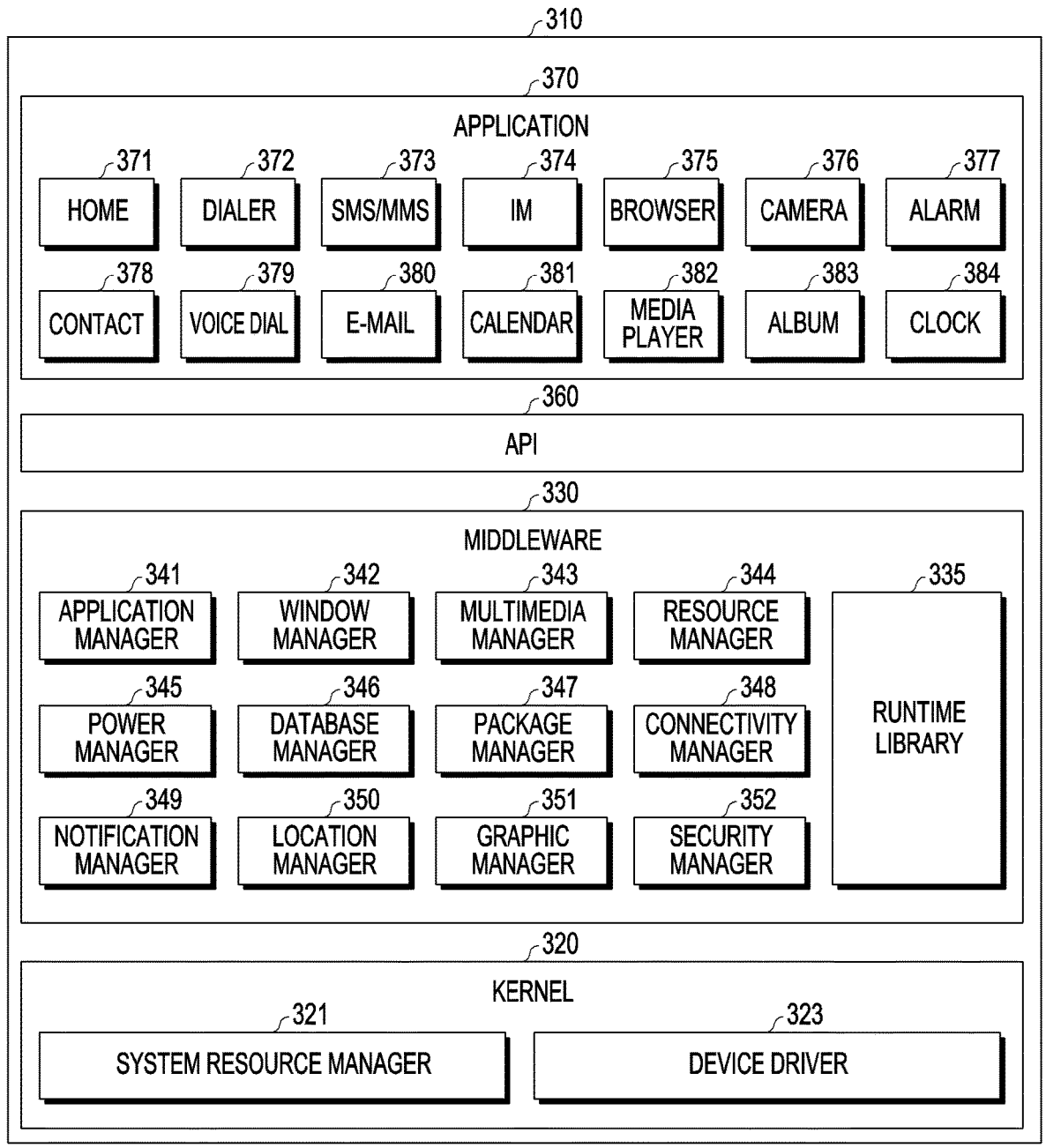
FIG. 3 is a block diagram illustrating a program module according to various embodiment of the present invention.

FIG. 3 is a block diagram illustrating a program module according to various embodiments. According to an embodiment of the present disclosure, the program module 310 (e.g., the program 140) may include an operating system (OS) controlling resources related to the electronic device (e.g., the electronic device 101) and/or various applications (e.g., the application processor 147) driven on the operating system. The operating system may include, e.g., Android™, iOS™, Windows™, Symbian™, Tizen™, or Bath™. Referring to FIG. 3, the program module 310 may include a kernel 320 (e.g., the kernel 141), middleware 330 (e.g., the middleware 143), an API 360 (e.g., the API 145), and/or an application 370 (e.g., the application program 147). At least a part of the program module 310 may be preloaded on the electronic device or may be downloaded from an external electronic device (e.g., the electronic devices 102 and 104 or server 106).

The kernel 320 may include, e.g., a system resource manager 321 or a device driver 323. The system resource manager 321 may perform control, allocation, or recovery of system resources. According to an embodiment of the present disclosure, the system resource manager 321 may include a process managing unit, a memory managing unit, or a file system managing unit. The device driver 323 may include, e.g., a display driver, a camera driver, a Bluetooth driver, a shared memory driver, a USB driver, a keypad driver, a Wi-Fi driver, an audio driver, or an inter-process communication (IPC) driver. The middleware 330 may provide various functions to the application 370 through the API 360 so that the application 370 may use limited system resources in the electronic device or provide functions jointly required by applications 370. According to an embodiment of the present invention, the middleware 330 may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, or a security manager 352.

The runtime library 335 may include a library module used by a compiler in order to add a new function through a programming language while, e.g., the application 370 is being executed. The runtime library 335 may perform input/output management, memory management, or arithmetic function processing. The application manager 341, for example, may manage the life cycle of the application 370. The window manager 342 may manage GUI resources used on the screen. The multimedia manager 343 may grasp formats necessary to play media files and use a codec appropriate for a format to perform encoding or decoding on media files. The resource manager 344 may manage the source code or memory space of the application 370. The power manager 345 may manage, e.g., the capacity, temperature, or power of the battery and provide power information necessary for the operation of the electronic device using a corresponding piece of information of such. According to an embodiment of the present invention, the power manager 345 may interwork with a basic input/output system (BIOS). The database manager 346 may generate, search, or vary a database to be used in the applications 370. The package manager 347 may manage installation or update of an application that is distributed in the form of a package file.

The connectivity manager 348 may manage, e.g., wireless connectivity. The notification manager 349 may provide an event, e.g., arrival message, appointment, or proximity alert, to the user. The location manager 350 may manage, e.g., locational information on the electronic device. The graphic manager 351 may manage, e.g., graphic effects to be offered to the user and their related user interface. The security manager 352 may provide system security or user authentication, for example. According to an embodiment of the present invention, the middleware 330 may include a telephony manager for managing the voice or video call function of the electronic device or a middleware module able to form a combination of the functions of the above-described elements. According to an embodiment of the present invention, the middleware 330 may provide a module specified according to the type of the operating system. The middleware 330 may dynamically omit some existing components or add new components. The API 360 may be a set of, e.g., API programming functions and may have different configurations depending on operating systems. For example, in the case of Android or iOS, one API set may be provided per platform, and in the case of Tizen, two or more API sets may be offered per platform.

The application 370 may include an application that may provide, e.g., a home 371, a dialer 372, an SMS/MMS 373, an instant message (IM) 374, a browser 375, a camera 376, an alarm 377, a contact 378, a voice dial 379, an email 380, a calendar 381, a media player 382, an album 383, or a clock 384, a healthcare app (e.g., measuring the degree of workout or blood sugar), or provision of environmental information (e.g., provision of air pressure, moisture, or temperature information). According to an embodiment of the present invention, the application 370 may include an information exchanging application supporting information exchange between the electronic device and an external electronic device. Examples of the information exchange application may include, but is not limited to, a notification relay application for transferring specific information to the external electronic device, or a device management application for managing the external electronic device. For example, the notification relay application may transfer notification information generated by other application of the electronic device to the external electronic device or receive notification information from the external electronic device and provide the received notification information to the user. For example, the device management application may install, delete, or update a function (e.g., turn-on/turn-off the external electronic device (or some elements) or adjusting the brightness (or resolution) of the display) of the external electronic device communicating with the electronic device or an application operating on the external electronic device. According to an embodiment of the present invention, the application 370 may include an application (e.g., a healthcare application of a mobile medical device) designated according to an attribute of the external electronic device. According to an embodiment of the present invention, the application 370 may include an application received from the external electronic device. At least a portion of the program module 310 may be implemented (e.g., executed) in software, firmware, hardware (e.g., the processor 210), or a combination of at least two or more thereof and may include a module, program, routine, command set, or process for performing one or more functions.

Figure 4A:
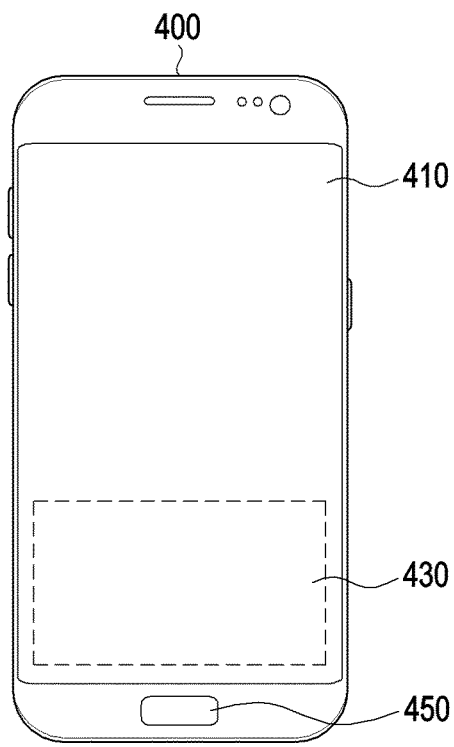
FIGS. 4A and 4B are example views illustrating a display including a biometric sensor according to various embodiments of the present invention.
Figure 4B:
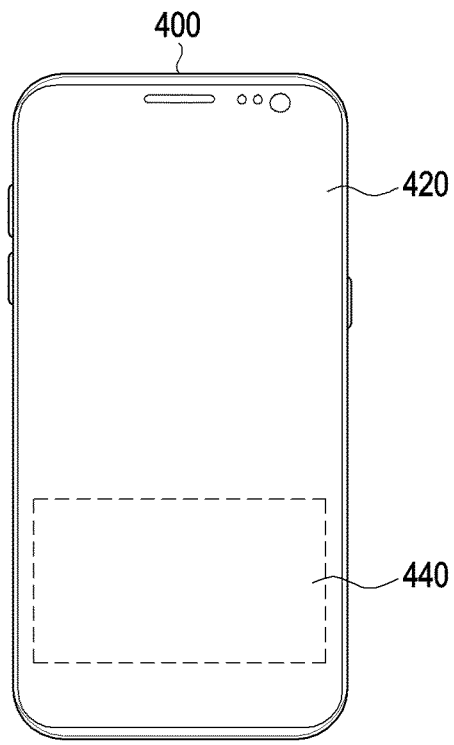

FIGS. 4A and 4B are example views illustrating a display including a biometric sensor according to various embodiments of the present invention.

Referring to FIG. 4A, an electronic device 400 may include a display 410 and an input button 450 provided separately from the display 410. The electronic device 400 may include a biometric sensor 420 (e.g., a fingerprint sensor) for recognizing biometric information (e.g., fingerprint information) in at least a portion of the display 410. As the biometric sensor 420 is formed in at least a portion (e.g., the active area of the display) or black matrix area of the display 410, the processor 120 of the electronic device 400 may obtain biometric information related to the user using a user input detected through the panel 262 of the display 410. Further, referring to FIG. 4B, an electronic device 400 may have a display 420 on the whole front surface of the electronic device 400 and may not include a separate physical input button. According to an embodiment, the electronic device 400 may have a biometric sensor 440 in at least a partial area of the display 420 and display the area which the biometric sensor 440 occupies on the display 420.

Figure 5:
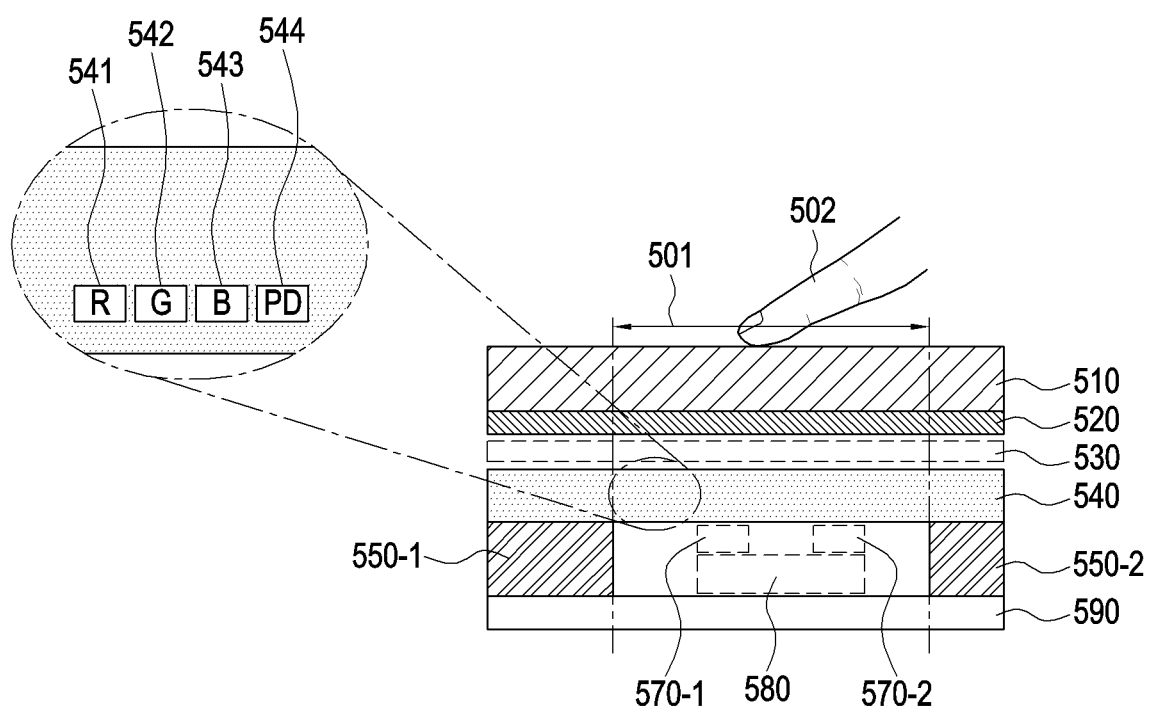
FIG. 5 is an example view illustrating a biometric sensor mounting structure to detect the user's biometric information in at least a portion of a display of an electronic device according to various embodiments of the present invention.

FIG. 5 is an example view illustrating a biometric sensor mounting structure to detect the user's biometric information in at least a portion of a display of an electronic device according to various embodiments of the present invention.

According to various embodiments of the present invention, an electronic device 201 may include a cover glass 510, a biometric sensor 530, 544, or 580, a display 540, and a PCB 590. Like the biometric sensor 580, the biometric sensor 530, 544, or 580 may be formed in a partial area 501 (e.g., one or more areas) of the display 540 to detect the user's input 502. Like the biometric sensor 530, the biometric sensor 530, 544, or 580 may be formed in the entire area (e.g., the active area of the display) of the display 540 to detect the user's input 502 via the entire area of the display 540. Like the biometric sensor 544 which is an optical biometric recognition sensor, the biometric sensor 530, 544, or 580 may detect the user's input 502 using, as a light source, light emitted from the display module. The glass 510 and the biometric sensor 530 may be attached together through an adhesive 520. As in the case of the biometric sensor 580 which is equipped not in the entire area but in a partial area, the cover glass 510 and the display 540 may be attached together through the adhesive 520.

According to various embodiments of the present invention, the electronic device may further include structures 550-1 and 550-2 to secure a mounting space for the biometric sensor 580. At this time, the structures 550-1 and 550-2 may form part of a sealing structure for protecting the fingerprint sensor 580.

According to various embodiments of the present invention, a biometric sensor 544 (photo diode), which is a sort of optical sensor capable of detecting biometric information, may be formed in one surface (e.g., an upper surface) (e.g., a separate layer 530 over one surface of the display or at least a partial area of the surface where pixels 541, 542, and 543 of the display are formed) of the display 540. According to another embodiment, a biometric sensor 580 may be formed on another surface (e.g., the rear surface of the display) of the display. The biometric sensor 530, 544, or 580 may include, e.g., an optical image sensor, an ultrasonic transmitting/receiving module, or a capacitive transmitting/receiving electrode pattern.

According to various embodiments of the present invention, the biometric sensor 530 may be formed of a capacitive transmitting/receiving electrode pattern and may be formed of a transparent electrode to raise the transmittance of light emitted from the display 540. According to another embodiment, the biometric sensor 530 may also include an ultrasonic transmitting/receiving module.

According to various embodiments of the present invention, the electronic device may include a biometric sensor 580 on the rear surface of the display. Elastomers 570-1 and 570-2 (e.g., sponge or rubber) may be formed between the display 540 and the biometric sensor 580 to mitigate impacts between the biometric sensor 580 and the display 540 or prevent influx of a foreign body. According to an embodiment, the biometric sensor 580 may include an image sensor. For example, the image sensor may output light (e.g., visible light, infrared, or ultraviolet light) emitted from a light source (e.g., the display 540 or an IR LED) to the user's fingerprint and detect the light reflected by the user's fingerprint.

Figure 6:
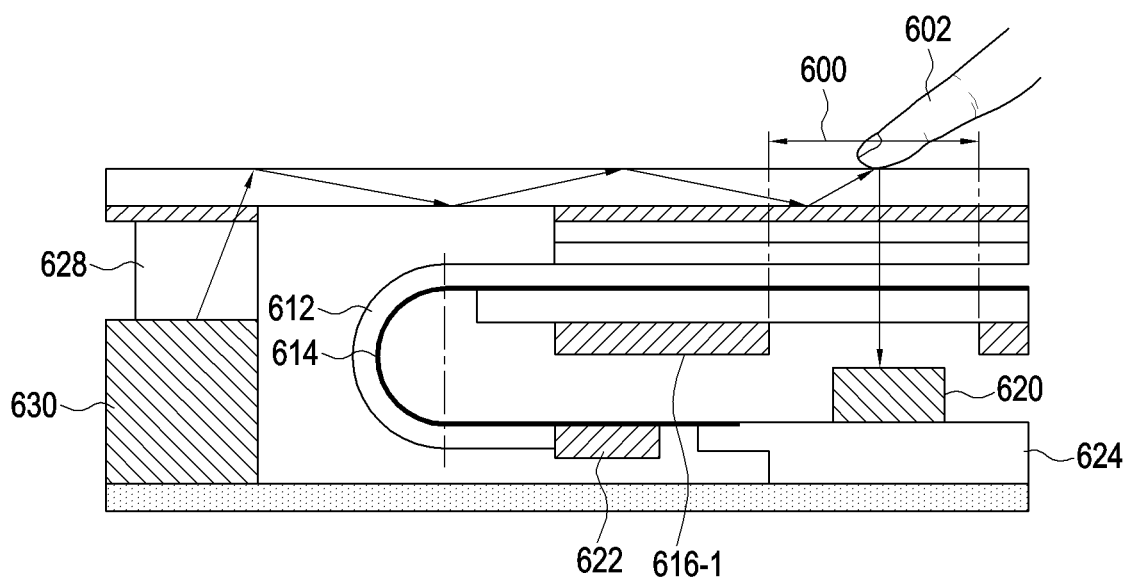
FIG. 6 is an example view illustrating a display structure including an IR light source and a display light source according to various embodiments of the present invention.

FIG. 6 is an example view illustrating a display structure including an IR light source and a display light source according to various embodiments of the present invention.

Referring to FIG. 6, if the user's input 602 is detected through a partial area 600 of the display of the window 604, the processor 120 may obtain the user's biometric information (e.g., fingerprint information) corresponding to the user's input 602 through the biometric sensor 620. The biometric sensor 620 may obtain light reflected by the user's fingerprint using the display-based light source (e.g., R, G, B pixel) to obtain the user's fingerprint information. According to an embodiment, the electronic device may obtain a fingerprint using infrared light emitted from the IR LED 630. For example, the infrared light emitted from the IR LED 630 may be totally reflected inside the window through a refracting part 628 to at least partially change the path of the infrared light, and the totally reflected light may be reflected by the user's body part, and the biometric sensor 620 may detect the totally reflected light.

Figure 7:
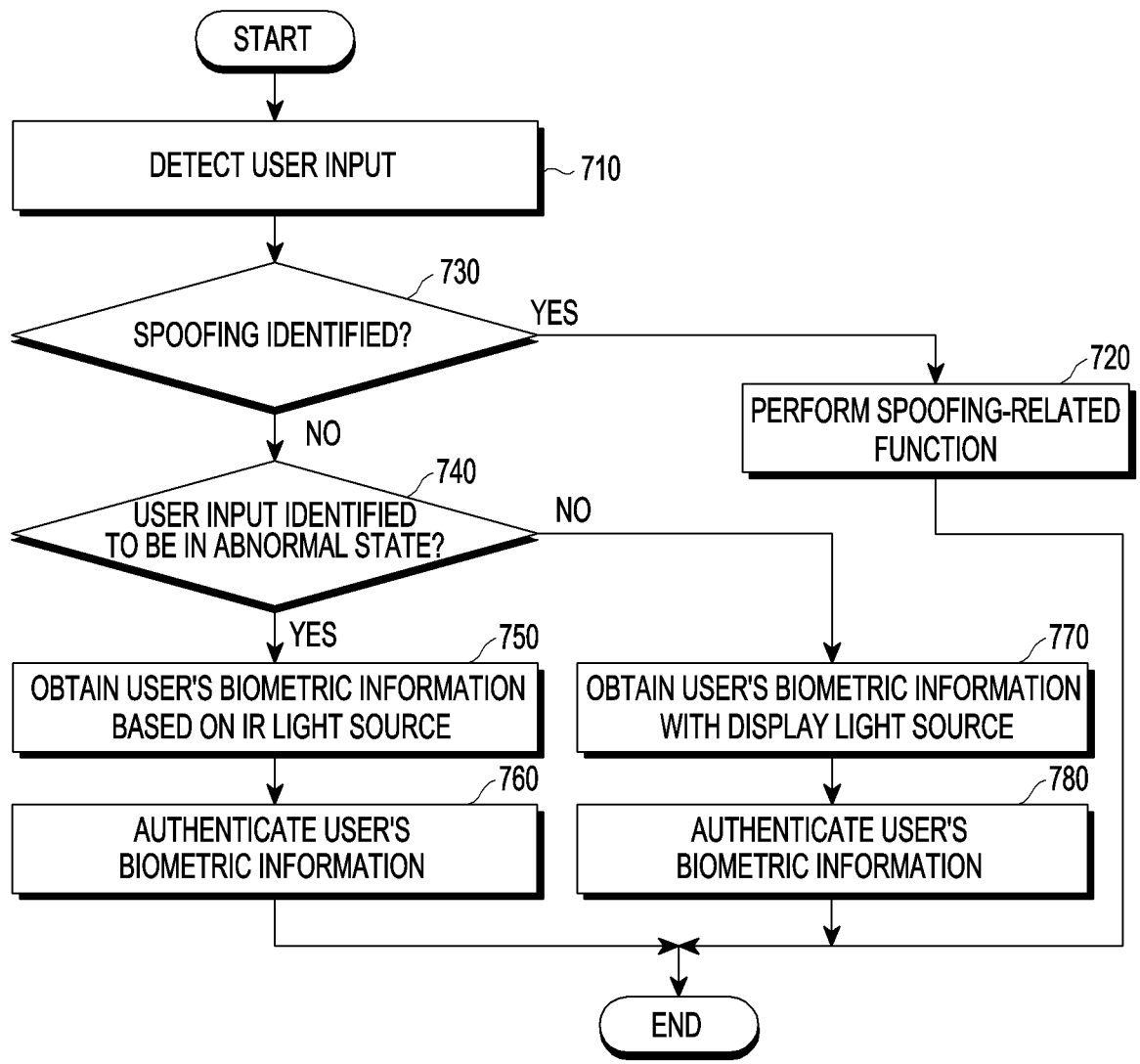
FIG. 7 is an example flowchart illustrating an algorithm to control a biometric sensor according to various embodiments of the present invention.

FIG. 7 is an example flowchart illustrating an algorithm to control a biometric sensor according to various embodiments of the present invention.

According to various embodiments of the present invention, an electronic device may include a biometric sensor to obtain biometric information related to the user, a light emitting circuit including a first light source to emit light with a designated band, a display panel 262 including a second light source to emit light including one or more pixels, and a processor 120. For example, the first light source may be an IR light source, and the second light source may be a display light source. The processor 120 may control the first light source and the second light source. Specifically, the processor 120 may control the turn-on and turn-off of the first light source or second light source to obtain the user's biometric information. The processor 120 may turn on the first light source or second light source before obtaining the user's biometric information and, when obtaining the biometric information is ended, turn off the first light source or second light source.

According to various embodiments of the present invention, the processor 120 of the electronic device may identify context information related to the user, select at least one corresponding light source of the first light source and the second light source based on, at least, the context information, and obtain the biometric information through the biometric sensor using the at least one light source selected. In operation 710, the processor 120 may detect the user's input to the touch panel of the display panel. For example, the user's input may be an input detected in various manners, such as a touch input or force input. If the user's input is detected, the processor 120 may identify whether there has been spoofing so as to identify whether the input is one made by the user. Spoofing is a way to hack an electronic device to obtain a user's information through an arbitrarily formed website. The operation of the electronic device may denote an operation to determine whether the user's fingerprint is a human fingerprint or a forged fingerprint for the purpose of reinforcing security.

The operation to identify spoofing may be performed before identifying an abnormal state of the user's input, but the present invention is not limited thereto, and the operation may be performed after identifying an abnormal state or, depending on the security level, may be omitted. Spoofing performed by the electronic device is described below in detail with reference to FIGS. 13 and 14.

In operation 730, when the input is not one made by a user but is spoofing, the processor 120 may perform a spoofing-related function. The spoofing-related function is obvious to a skilled artisan and no detailed description thereof is presented. Meanwhile, upon detecting that the user's input is not spoofing, the processor 120 may identify whether the user's input is in an abnormal state in operation 740. Abnormal may mean a state in which the user's body is wet or dry when the user makes a touch input or force input to the display panel using the user's body, e.g., his or her finger. Upon determining that the user's input is in the abnormal state, the processor 120 may obtain the user's biometric information based on the IR light source in operation 750. Specifically, the processor 120 may turn on the IR light source before obtaining biometric information, detect the infrared (IR) light emitted from the IR light source and reflected by the user's body part using the biometric sensor, and obtain the user's biometric information, e.g., fingerprint information, using the reflected light reflected. In operation 760, the processor 120 may authenticate the biometric information using the user's biometric information obtained. Meanwhile, upon determining that the user's input is normal, the processor 120 may obtain the user's biometric information using the display light source in operation 770. Normal may collectively refer to cases where the user's fingerprint is not in the abnormal state or the display light source is sufficient to perform fingerprint recognition without the need for an IR light source. The processor 120 may turn on the display light source before obtaining biometric information and, if light from the display light source is reflected by the user's body part, the processor 120 may detect the reflected light using the biometric sensor. The processor 120 may generate and obtain the user's biometric information using the reflected light detected by the biometric sensor and authenticate the user's biometric information in operation 780.

Figure 8:
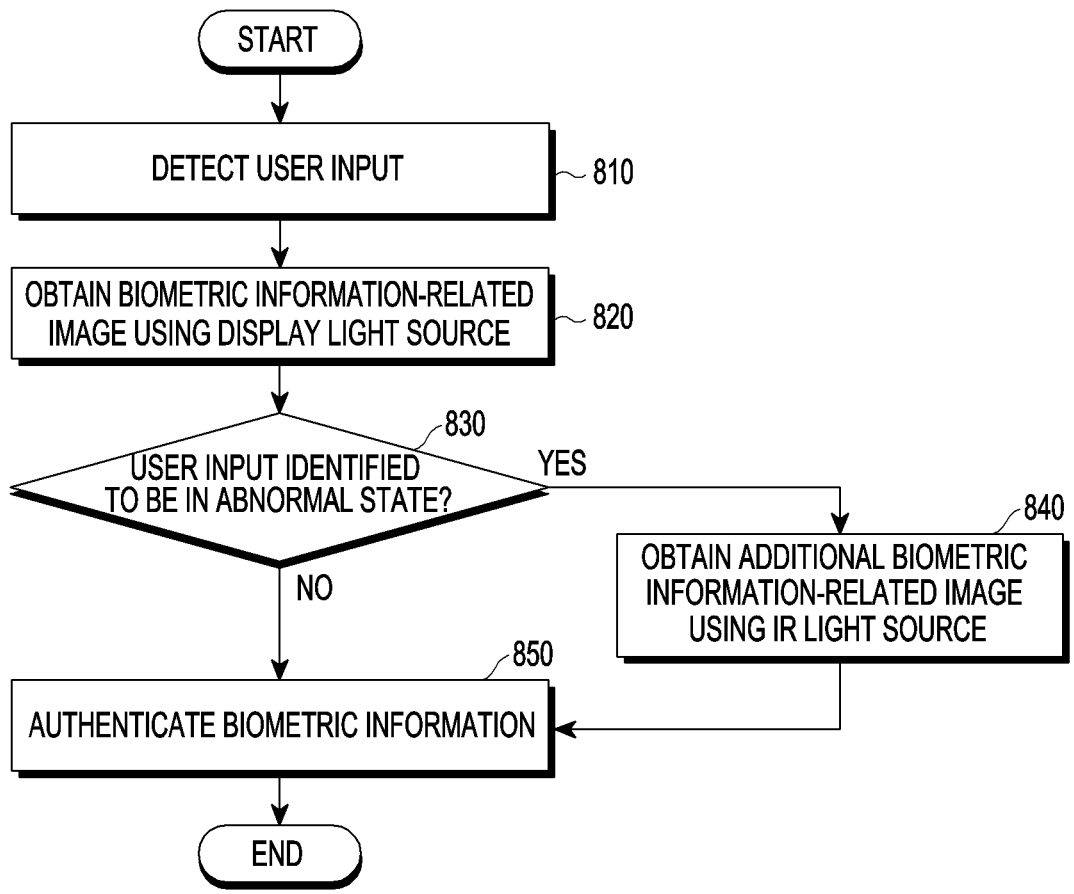
FIG. 8 is an example flowchart illustrating an algorithm to identify an abnormal state of a user input according to another embodiment of the present invention.

FIG. 8 is an example flowchart illustrating an algorithm to identify an abnormal state of a user input according to another embodiment of the present invention.

According to various embodiments of the present invention, the processor 120 may detect the user's input in operation 810. The processor 120 may obtain an image related to the biometric information using the display light source in operation 820. For example, to obtain biometric information, the processor 120 may turn on the display light source and secure, through the display, a light source capable of performing fingerprint recognition via a method (e.g., a high brightness mode (HBM)) to raise the brightness of a partial area of the display. If light from the display light source is reflected by the user's body part, the processor 120 may detect the reflected light using the biometric sensor. The processor 120 may obtain the user's biometric information, e.g., finger image, using the reflected light. If the operation of recognizing the user's fingerprint is done, the processor 120 may control the display light source to turn off. The electronic device may perform fingerprint recognition in various image analysis schemes based on the fingerprint image. For example, the electronic device may distinguish between the normal state and the abnormal state based on an image obtained via various schemes, e.g., spatial frequency, histogram, or contrast ratio.

In the electronic device according to various embodiments of the present invention, the context information may include information about whether the first light source is additionally needed to obtain the biometric information based on the state of the image obtained using the biometric sensor. In the electronic device according to various embodiments of the present invention, upon determining that the first light source is additionally needed, the processor 120 may be configured to obtain additional biometric information through the biometric sensor using the first light source.

Referring to FIG. 8, the processor 120 may identify whether the user's input is in the abnormal state in operation 830. The processor 120 may obtain context information based on the image obtained using the display light source. For example, the context information may be information about whether the user's input is in the abnormal state. As described above, the processor 120 may identify whether the user's input is in the abnormal state based on various image analysis schemes, such as spatial frequency, histogram, or contrast ratio. Upon determining that the user's input is in the abnormal state, the processor 120 may determine that an additional light source (e.g., an IR LED) is needed and obtain an additional image related to the biometric information using a second light source (e.g., an IR light source). For example, the processor 120 may turn on the IR LED and obtain an additional image associated with the user's biometric information based on the infrared light totally reflected through the IR LED. In operation 850, when the user's input is identified as being in the normal state in operation 830, the processor 120 may authenticate the user's biometric information using the image obtained in operation 820 or, when it is in the abnormal state, the processor 120 may authenticate the biometric information using the additional image obtained in operation 840.

Figure 9:
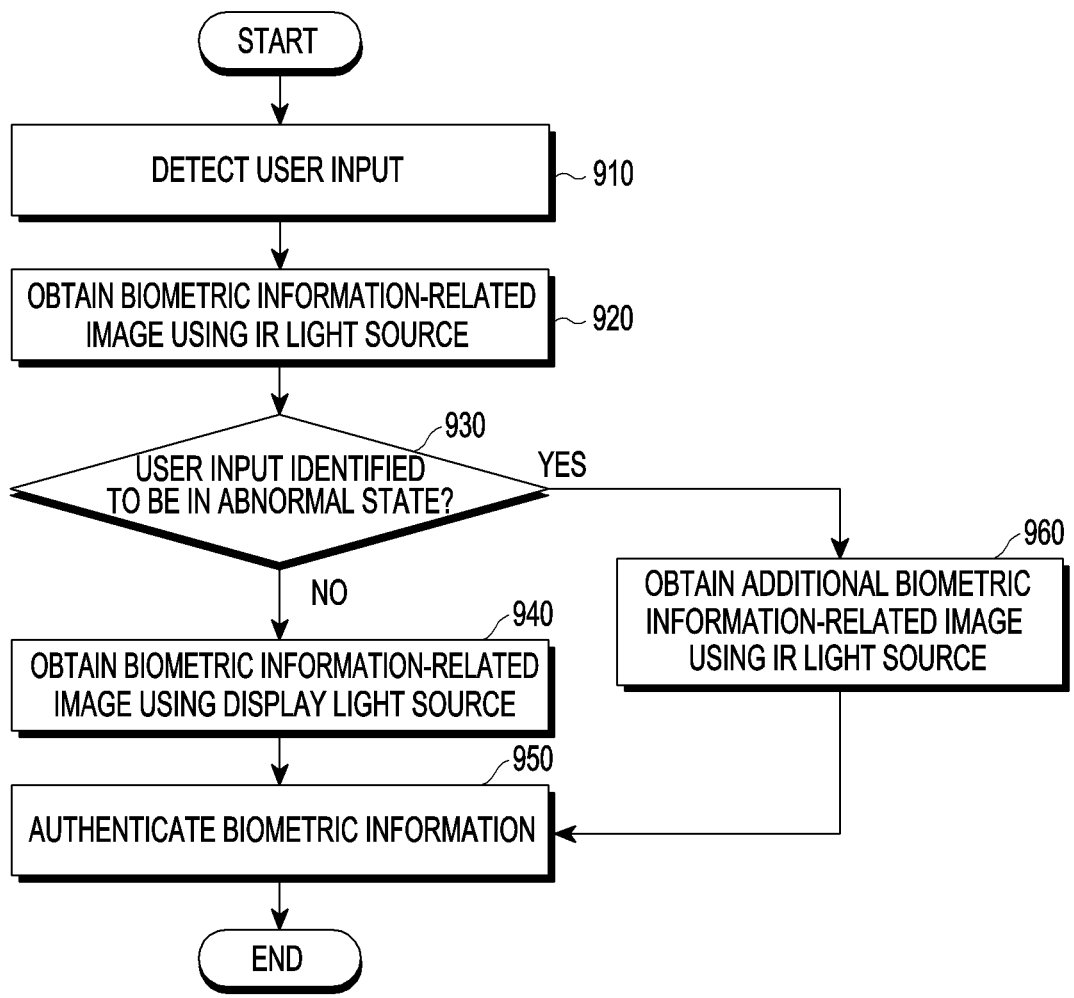
FIG. 9 is an example flowchart illustrating an algorithm to identify an abnormal state of a user input according to another embodiment of the present invention.

FIG. 9 is an example flowchart illustrating an algorithm to identify an abnormal state of a user input according to another embodiment of the present invention.

FIG. 9 is a view illustrating a method of grasping an abnormal state of a finger using an IR light source and turning on the IR LED light source depending on whether the finger is in the abnormal state to obtain a fingerprint-related image.

According to various embodiments of the present invention, the processor 120 may detect the user's input in operation 910. The processor 120 may obtain an image related to the biometric information using the IR light source in operation 920. Specifically, the processor 120 may turn on the IR light source to obtain biometric information and, if light emitted from the IR light source is reflected by the user's body part, the processor 120 may detect the reflected light using the biometric sensor. The processor 120 may obtain the user's biometric information, e.g., finger image, using the reflected light detected. If the operation of recognizing the user's fingerprint is done, the processor 120 may control the IR light source to turn off. The electronic device may perform fingerprint recognition in various image analysis schemes based on the fingerprint image. For example, the electronic device may distinguish between the normal state and the abnormal state based on an image obtained via various schemes, e.g., spatial frequency, histogram, or contrast ratio.

According to various embodiments of the present invention, the context information may include information about whether a first light source (e.g., an IR light source) is additionally needed to obtain the biometric information based on the state of the image obtained using the biometric sensor. Upon determining that the first light source is additionally needed, the processor 120 may be configured to obtain additional biometric information through the biometric sensor using the first light source. The processor 120 may identify whether the user's input is in the abnormal state in operation 930. The processor 120 may obtain context information based on the image obtained using the display light source. For example, the context information may be information about whether the user's finger is in the abnormal state, e.g., when the finger is wet or dry. As described above, the processor 120 may identify whether the user's input is in the abnormal state based on various image analysis schemes, such as spatial frequency, histogram, or contrast ratio. Upon determining that the user's input is in the abnormal state, the processor 120 may determine that an IR light source is needed and obtain an additional image related to the biometric information using an IR light source in operation 960. For example, the processor 120 may turn on the IR LED and obtain an additional image associated with the user's biometric information based on the infrared light totally reflected through the IR LED. In operation 940, upon determining that fingerprint recognition may be performed using the display light source, as the case where the user's input is identified as being in the normal state in operation 930, the processor 120 may obtain an image related to the biometric information using the display light source. In operation 950, the user's biometric information may be authenticated or, when it is in the abnormal state, biometric information may be authenticated using the additional information obtained in operation 940.

Figure 10A:
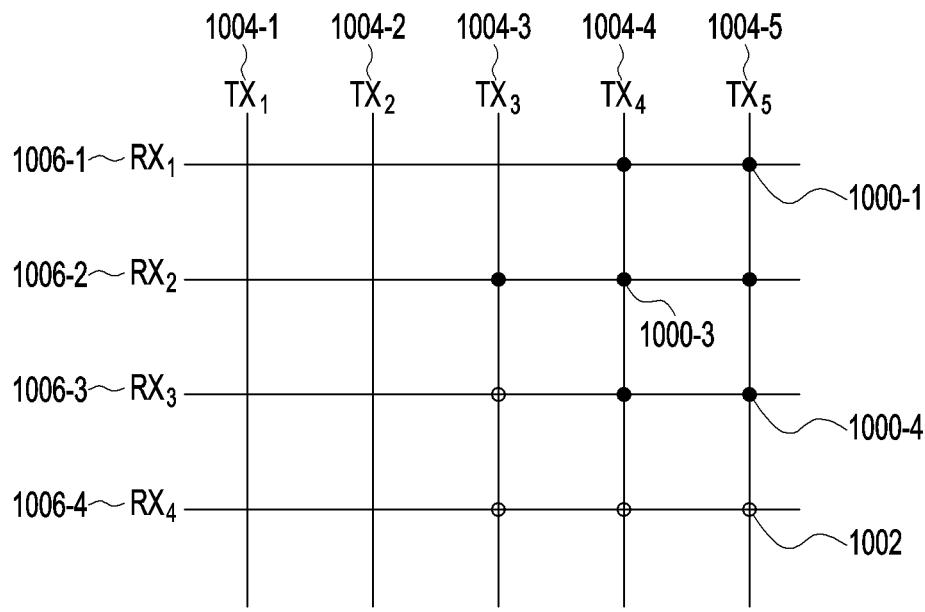
FIG. 10A is an example view illustrating a configuration of identifying the capacitance of a touch panel according to various embodiments of the present invention.
Figure 10B:
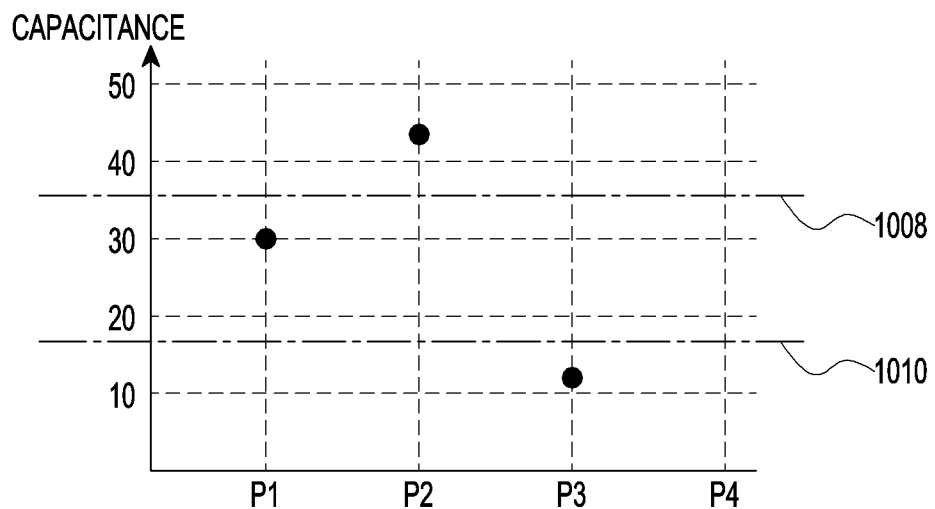
FIG. 10B is a graph illustrating a configuration of identifying the capacitance of FIG. 9A according to various embodiments of the present invention.

FIG. 10A is an example view illustrating a configuration of identifying the capacitance of a touch panel according to various embodiments of the present invention. FIG. 10B is a graph illustrating a configuration of identifying the capacitance of FIG. 10A according to various embodiments of the present invention.

FIG. 10A is a view illustrating a touch panel to identify the user's input in a wet state based on a variation in capacitance of the user's finger upon touching by the user's input.

According to various embodiments of the present invention, when the user's input is applied to the touchscreen display, the context where the user's body part is wet may be identified via a variation in capacitance due to moisture detected on the touch panel. The IR light source or display light source may be selectively controlled based on the variation in capacitance. The touch panel of the electronic device may be constituted of wires TX1, 2, 3, 4, and 5 (1004-1, 1004-2, 1004-3, 1004-4, and 1004-5) to emit a TX signal and wires RX1, 2, 3, and 4 (1006-1, 1006-2, 1006-3, and 1006-4) to obtain a receiving signal by the TX. When the user's input is detected through the touchscreen display, the capacitance at the touched point may be obtained. For example, the processor 120 may allow the electronic device to recognize P1 (1000-1), P2 (1000-3), and P3 (1000-4) as touched points and P4 (1002) as a point where no user input is detected. At this time, whether the user's finger is wet may be identified by identifying capacitances for P1, P2, and P3. Permittivity may be varied depending on the degree to which the user's body part is wet, and the processor 120 may measure the variation in capacitance based on the varying permittivity. For example, if the permittivity of water is 80 and the permittivity of skin is 50, permittivity may be measured depending on the state of the finger. A formula to obtain the capacitance depending on the permittivity is as follows.

[85]

$$\text{Capacitance} = \varepsilon \frac{A}{d} \quad \text{[Equation 1]}$$

Referring to Equation 1, the capacitance may be calculated by permittivity $\varepsilon$, touched area A, and distance d.

In a case where the capacitances corresponding to P1, P2, and P3 are obtained by Equation 1, such a graph as shown in FIG. 10B may be obtained.

According to various embodiments of the present invention, a touch panel may be included which is disposed on the display. The context information may include the capacitance of the touch panel according to the user's input detected to obtain the user's biometric information. In a case where the capacitance of the touch panel where the user's input is detected is higher than a preset threshold, the processor 120 may obtain the biometric information through the biometric sensor using the first light source.

According to various embodiments of the present invention, the processor 120 may identify the capacitance of at least one point of the touch panel where the user's input is detected and compare the capacitance of the at least one point with the preset threshold.

According to various embodiments of the present invention, the processor 120 may set a threshold to determine the abnormal state of the user's input. The processor 120 may set a first threshold and a second threshold to detect the user's body which is wet. For example, if the capacitance at the touched point is not less than the first threshold, the processor 120 may determine that the user's body is wet and thus the user's input is in the abnormal state. In a case where the capacitance at the touched point is not more than the first threshold and not less than the second threshold, the processor 120 may detect that the user's input is in the normal state and, in a case where the capacitance at the touched point is not more than the second threshold, the processor 120 may identify that the user's body is dry and the user's input is in the abnormal state. According to an embodiment, the abnormal state may be when the capacitance of the touch panel by the input of the user's body is not less than the first threshold and not more than the second threshold. In the example of FIG. 10B, in the case of the touched point P1, the capacitance is not less than the second threshold (1010) and not more than the first threshold (1008) and, thus, it is determined to be in the normal state. In the case of P2, the capacitance is not less than the first threshold 1008 and, thus, it is in the abnormal state as the user's body being wet. In the case of P3, the capacitance is not more than the second threshold 1010 and, thus, it is determined to be in the abnormal state as the user's body being dry.

Figure 11:
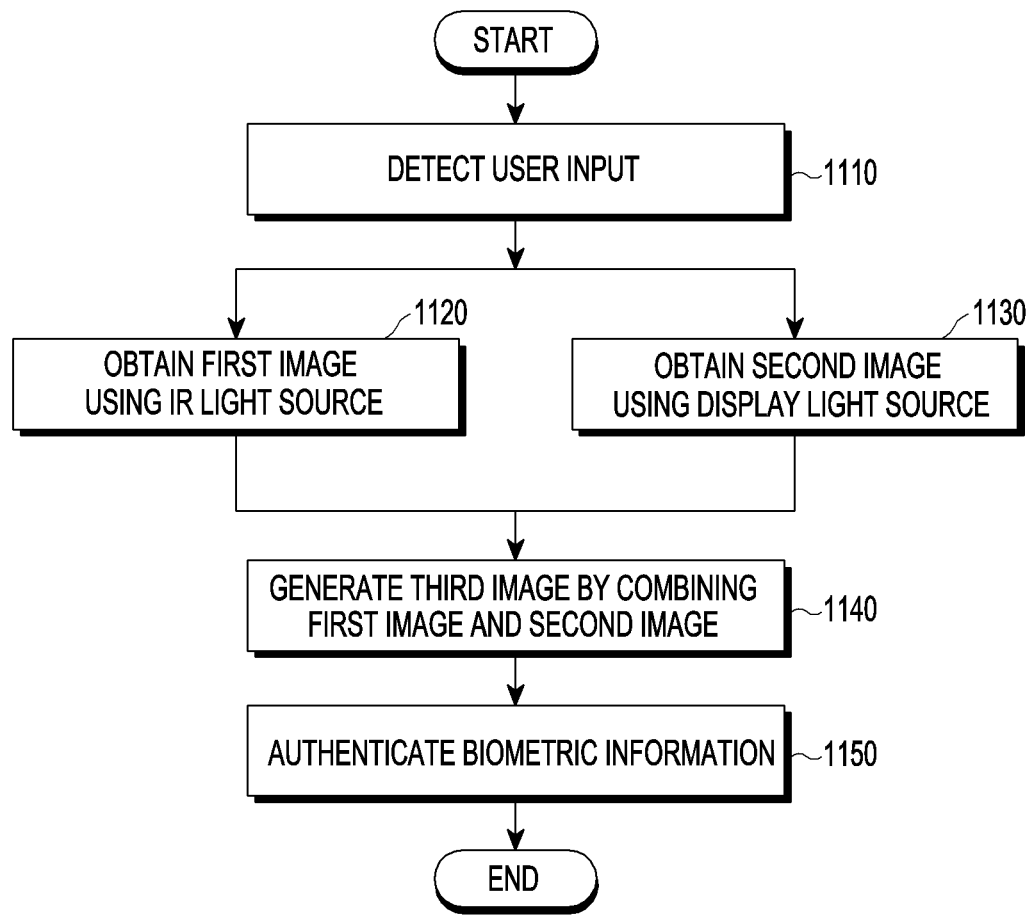
FIG. 11 is an example view illustrating a biometric sensor control algorithm according to various embodiments of the present invention.

FIG. 11 is an example view illustrating a biometric sensor control algorithm according to various embodiments of the present invention.

According to various embodiments of the present invention, A more proper image for obtaining a fingerprint may be generated using a fingerprint image obtained using both the IR light source and the display light source without prior determination on the abnormal state of the user's input, and fingerprint authentication may be performed. In operation 1110, the processor 120 may detect the user's input to the touchscreen display. In operations 1120 and 1130, the processor 120 may generate a first image and a second image using the IR light source and the display light source. The operation of generating the first image and the operation of generating the second image are not limited to a specific order, and the second image may be obtained earlier than the first image. In operation 1140, the processor 120 may identify the first image or the second image and may generate a third image which may be used for fingerprint authentication based on an appropriate one of various image analysis schemes, such as spatial frequency, histogram, or contrast ratio. Although not shown, without generating the third image, the processor 120 may select an image available for fingerprint authentication of the first image and the second image based on various image analysis methods described above and authenticate the biometric information. In operation 1150, the processor 120 may authenticate the biometric information using the generated third image.

Figure 12:
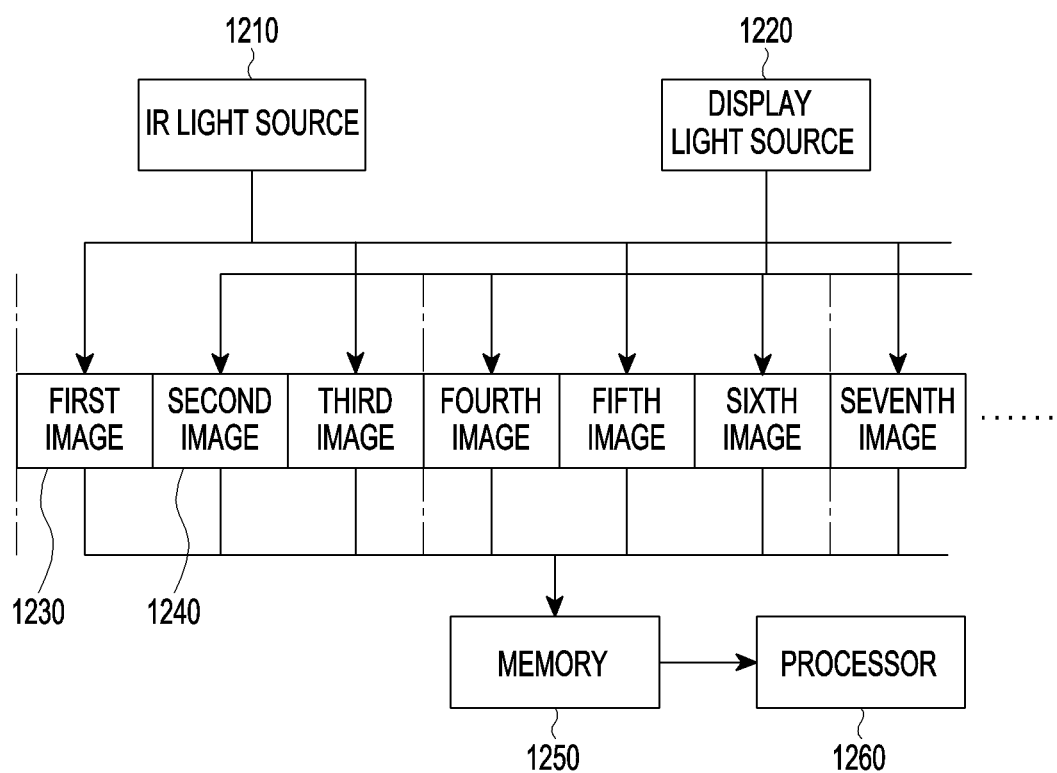
FIG. 12 is an example view illustrating image synthesis using an IR light source and a display light source according to various embodiments of the present invention.

FIG. 12 is an example view illustrating image synthesis using an IR light source and a display light source according to various embodiments of the present invention.

FIG. 12 illustrates a structure in which the first image or second image obtained by the image sensor is stored in an image buffer by the scheme of FIG. 11.

Referring to FIG. 12, a processor 1260 (e.g., the processor 120 of FIG. 1) may store a first image 1230 obtained through a biometric sensor using an IR light source 1210 in a memory 1250. Further, the processor 1260 may store a second image 1240 obtained using a display light source 1220 in the memory 1250. The processor 1260 may obtain the first image 1230 during a predetermined period and store the first image in the memory, and the processor 1260 may obtain the second image 1240 during a predetermined period and store the second image in the memory.

According to various embodiments of the present invention, the processor may continuously and repetitively obtain a third image, fourth image, and fifth image during a predetermined period and store them in the memory 1250. The processor 1260 may synthesize or select a fingerprint image using a plurality of images stored in the memory 1250. For example, the processor 1260 may select at least one of a fingerprint image based on an IR light source and an image based on the display light source and determine which one is an image for fingerprint authentication. According to various embodiments of the present invention, the processor 1260 may modify or correct an image to synthesize the first image 1230 or the second image 1240 through separate correction or filtering.

Figure 13:
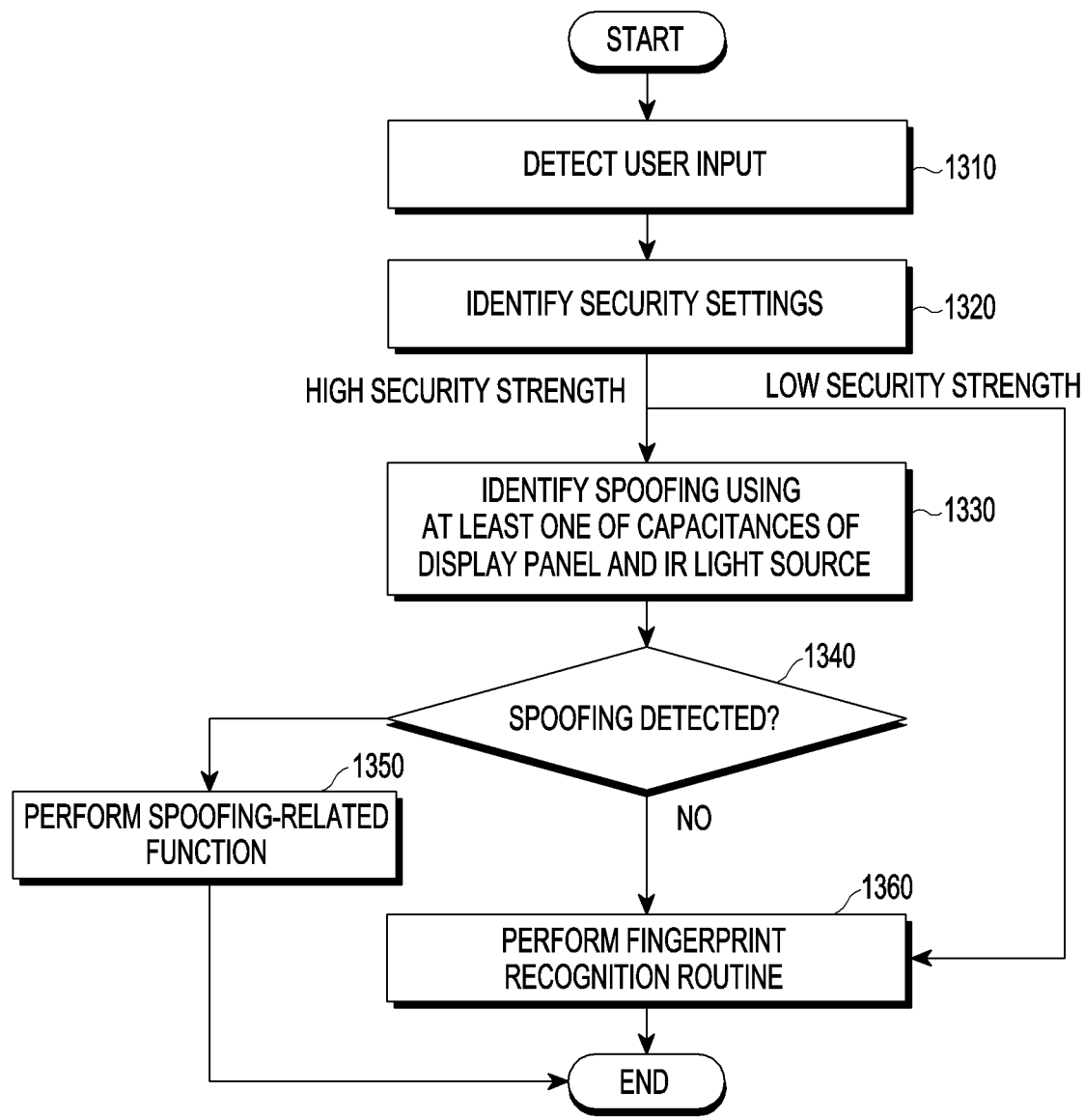
FIG. 13 is an example flowchart illustrating an algorithm to detect spoofing according to various embodiments of the present invention.

FIG. 13 is an example flowchart illustrating an algorithm to detect spoofing according to various embodiments of the present invention.

When an electronic device performs authentication using the user's fingerprint, various security threats may occur. For example, the user's fingerprint may be forged (e.g., by 3D printing or silicone molding) to attempt authentication. According to various embodiments of the present invention, the electronic device may include a method and structure to prevent such security threats.

Referring to FIG. 13, according to an embodiment, a processor (e.g., the processor 120 of FIG. 1) may detect the user's input to the touchscreen display via the sensor in operation 1310. In operation 1320, the processor (e.g., the processor 120 of FIG. 1) may identify security settings. For example, the processor (e.g., the processor 120 of FIG. 1) may identify whether detection of spoofing is needed based on environment information, e.g., the user's settings (security strength) or the security strength of the application being used (e.g., a financial application or security-required application). For example, when the security strength is determined to be high according to the environment information, the processor (e.g., the processor 120 of FIG. 1) may identify spoofing using at least one of the capacitances of the IR light source and the touch panel in operation 1330.

According to various embodiments of the present invention, in a case where the security strength is determined to be low in user authentication, the processor (e.g., the processor 120 of FIG. 1) may perform a fingerprint recognition routine in operation 1360. For example, when screen unlock is performed using fingerprint input, for operations with a low security strength, operations 1330 and 1340 of identifying spoofing may be omitted to raise the speed of user authentication. According to various embodiments of the present invention, a spoofing identification operation may be set or released based on the user's position or the position of the electronic device by the processor (e.g., the processor 120 of FIG. 1). For example, the position of the electronic device may be obtained based on a GPS signal. When the obtained position of the electronic device is in a position that requires reinforced security in authenticating the user, the electronic device may automatically perform the spoofing identification operations 1330 and 1340 if the electronic device is located in a preset position. For example, when the user travels to a certain area, a particular village or building may be set to an area that requires reinforced security, and when the user's electronic device is located in the corresponding position, the processor (e.g., the processor 120 of FIG. 1) of the electronic device may automatically perform the spoofing identification operations 1330 and 1340. In operation 1340, the processor (e.g., the processor 120 of FIG. 1) may identify whether spoofing is detected.

According to various embodiments of the present invention, the processor (e.g., the processor 120 of FIG. 1) may perform the spoofing identification operation based on security settings. For example, the processor (e.g., the processor 120 of FIG. 1) may determine whether there is spoofing based on at least one of variations in the capacitance of the touchscreen panel where the user's touch is detected or the IR light source. The processor (e.g., the processor 120 of FIG. 1) of the electronic device may identify whether the object touching a partial area of the display is the user's actual finger or a finger forged with, e.g., silicone based on information obtained from variation in capacitance of the touchscreen panel or the IR light source.

According to various embodiments of the present invention, in a case where the touching object is doubtful for spoofing or determined to be spoofing by the spoofing identification operation, the processor (e.g., the processor 120 of FIG. 1) may perform a spoofing-related function in operation 1350. According to various embodiments of the present invention, upon determining that spoofing occurs through the spoofing-related processing function, the processor (e.g., the processor 120 of FIG. 1) may perform a security-related operation. For example, when the fingerprint recognized for bank account transfer is determined to be a spoofed fingerprint, upon attempting to access a specific number of times, the corresponding application may be locked, or an additional user authentication operation by a second fact (e.g., password) may be performed.

According to various embodiments of the present invention, in a case where the touching object is determined not to be spoofing, the processor (e.g., the processor 120 of FIG. 1) may perform a fingerprint recognition routine in operation 1360. In operation 1360, the processor (e.g., the processor 120 of FIG. 1) may perform the fingerprint recognition routine. The fingerprint recognition routine is the same as those described above in connection with FIGS. 4 to 12, and no detailed description thereof is given. If fingerprint recognition is complete, the electronic device may compare the user's fingerprint with a fingerprint image stored in the memory and perform authentication.

Figure 14A:
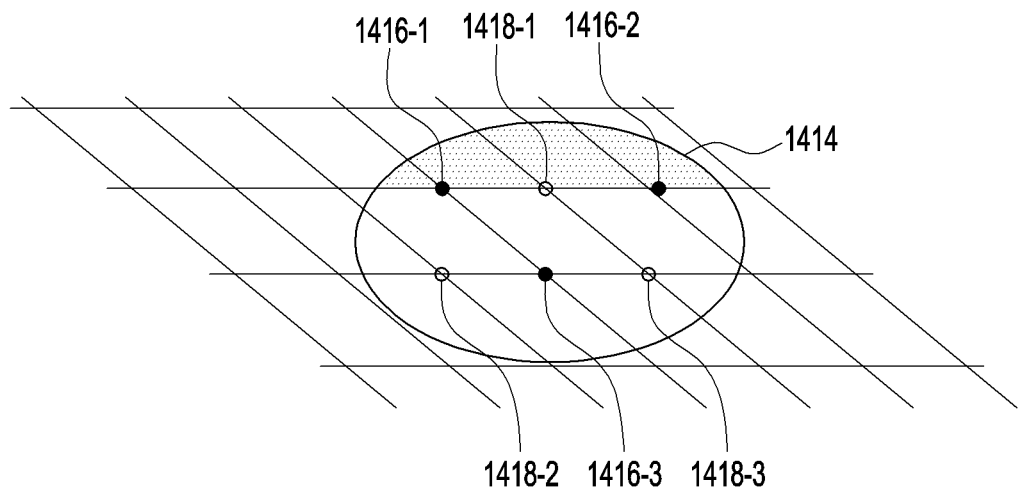
FIG. 14A is an example view illustrating a configuration of identifying the capacitance of a touch panel according to various embodiments of the present invention.
Figure 14B:
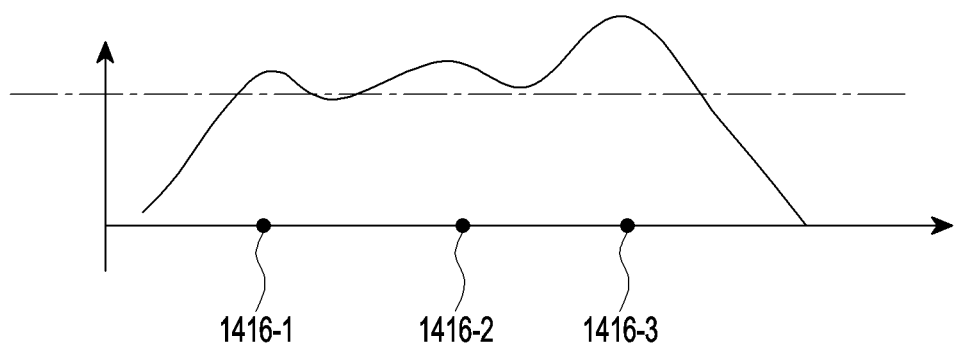
FIG. 14B is an example graph illustrating a configuration of identifying the capacitance of FIG. 14A according to various embodiments of the present invention.

FIG. 14A is an example view illustrating a configuration of identifying the capacitance of a touch panel according to various embodiments of the present invention. FIG. 14B is an example graph illustrating a configuration of identifying the capacitance of FIG. 14A according to various embodiments of the present invention.

According to various embodiments of the present invention, the electronic device may determine whether the user's fingerprint is forged according to the variation in capacitance corresponding to the user's body part obtained through at least a partial area of the display included in the electronic device. For example, the electronic device may grasp a variation in capacitance and identify whether the user's fingerprint is forged based on the variation in capacitance. For example, the permittivity of silicone prepared by 3D printing is different from the permittivity of the human body and, thus, the variation in capacitance may be varied.

Referring to FIG. 14A, the touchscreen panel of the electronic device may detect an area 1414 where the user's touch is detected. According to an embodiment, for fingerprint spoofing detection, at least some of touch detecting points included in the touch recognition area 1414, e.g., the points 1416-1 to 3 and 1418-1 to 3 where a touch is detected, may be set to spoofing detection points (e.g., 1416-1 to 3 of FIG. 14A). The electronic device may identify the variation in capacitance detected through the spoofing detection points 1416-1 to 3 and identify whether the fingerprint is one made by a real human being or forged. For example, the variation in capacitance corresponding to some spoofing detection points 1416-1 to 3 in the touch recognition area 1414 may be identified as shown in FIG. 14B. Referring to FIG. 14B, since the variation in capacitance at 1416-1 to 3 is determined to be higher than a threshold preset by the processor as the capacitance for an input of the true user, it may be identified that the user's input of FIG. 14B is not spoofing but is in fact the user's input.

Figure 15:
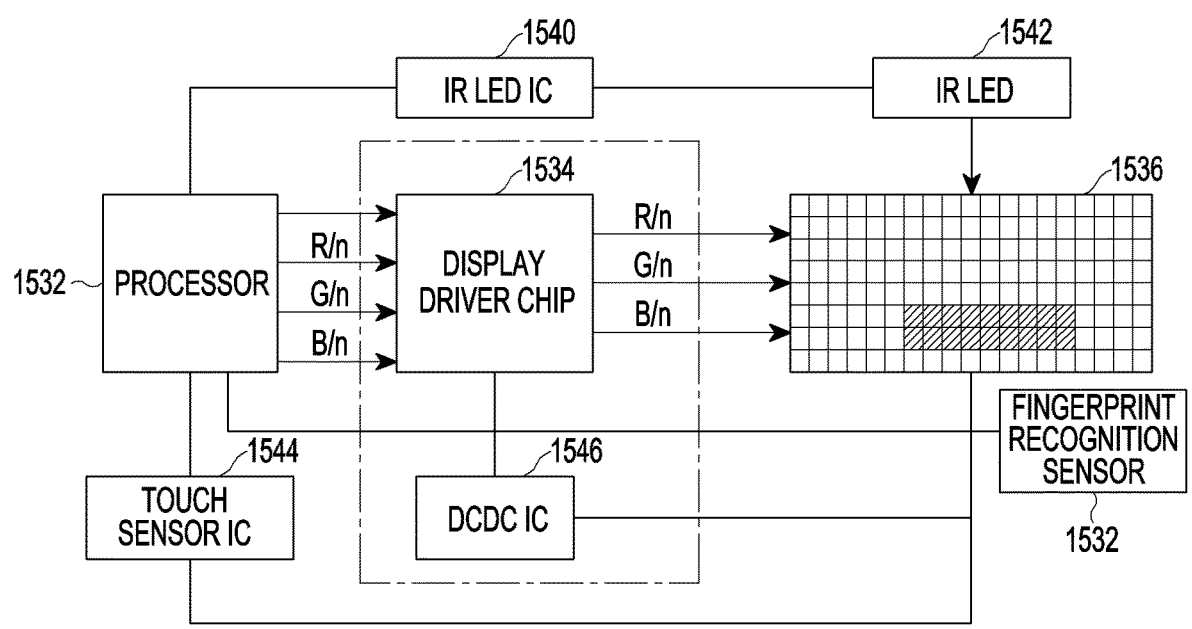
FIG. 15 is an example view illustrating a module of identifying capacitance to prevent spoofing according to various embodiments of the present invention.

FIG. 15 is an example view illustrating a module of identifying capacitance to prevent spoofing according to an embodiment of the present invention.

Referring to FIG. 15, a display driver chip (DDI) 1534 connected to a DC-DC integrated circuit (DCDC IC) 1546 may transmit some information about the user's input obtained using an infrared light emitting diode (IR LED) 1542 or light source of the touchscreen display 1536 to the processor 1532. The processor 1532 (e.g., the processor 120 of FIG. 1) may identify whether fingerprint information obtained using capacitance identification (analysis of variation in capacitance based on the touch sensor IC 1544) or the IR LED 1542 is human fingerprint information or a forged fingerprint. When the fingerprint is determined the processor 1532 to be a human fingerprint, the user's fingerprint information may be obtained through the fingerprint recognition sensor, and fingerprint authentication may be performed.

According to various embodiments of the present invention, the processor may store capacitance information about the user's normal touch and when a new touch input occurs, compare the capacitance information to the new touch input with the capacitance for the normal state, determine whether it matches or is similar to the normal state, and perform fingerprint authentication based on the similarity.

According to various embodiments of the present invention, different secure digital multimedia (SDM) processing schemes may be performed depending on the type of application running on the electronic device. For example, when the user's security strength is set to be low, the spoofing search function by the SDM may be skipped to quickly perform authentication. According to an embodiment, the security strength may be adjusted to differ depending on the type of application (e.g., a financial application or simple screen lock application).

Figure 16:
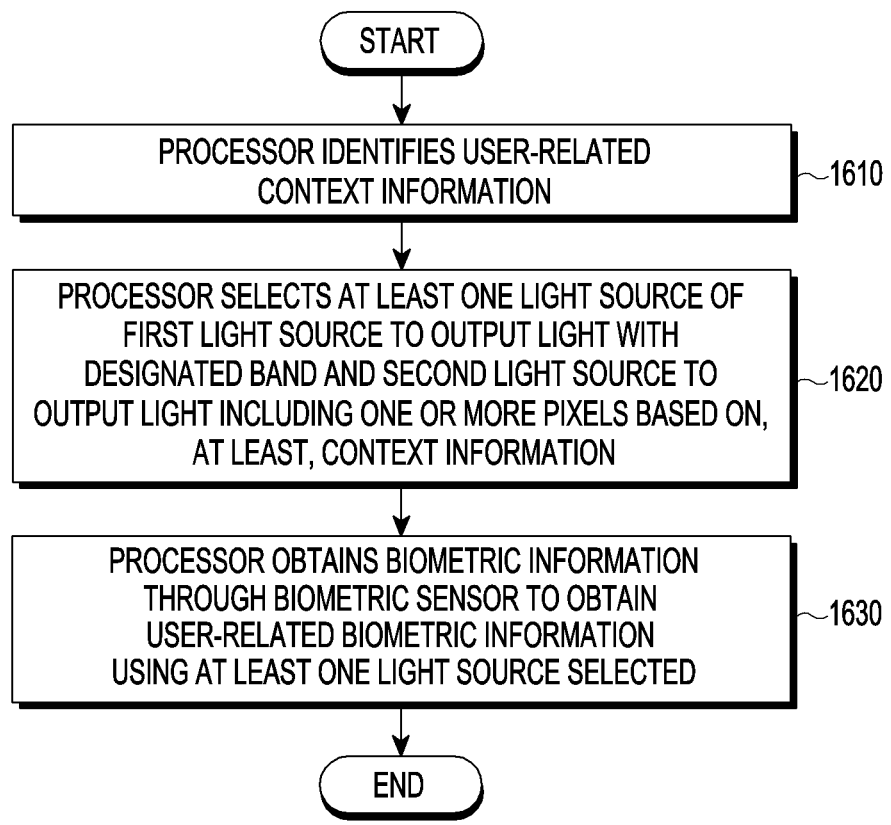
FIG. 16 is an example flowchart illustrating a method of controlling a biometric sensor according to various embodiments of the present invention.

FIG. 16 is an example flowchart illustrating a method of controlling a biometric sensor according to various embodiments of the present invention.

According to various embodiments of the present invention, in a method of controlling a biometric sensor, a processor (e.g., the processor 120 of FIG. 1) may identify context information related to the user in operation 1610. In operation 1620, the processor (e.g., the processor 120 of FIG. 1) may select at least one of a first light source to output light with a designated band and a second light source to output light including one or more pixels based on, at least, the context information. Further, in operation 1630, the processor (e.g., the processor 120 of FIG. 1) may obtain the biometric information through a biometric sensor to obtain biometric information related to the user using the at least one light source selected.

In a method of controlling the biometric sensor according to various embodiments of the present invention, the context information may include information about whether the first light source is additionally needed to obtain the biometric information based on the state of the image obtained using the biometric sensor. The method may include an operation in which, upon determining that the first light source is additionally needed, the processor (e.g., the processor 120 of FIG. 1) obtains additional biometric information through the biometric sensor using the first light source. In the method, the context information may include the capacitance of the touch panel according to the user's input detected to obtain the user's biometric information. The method may include an operation in which, when the capacitance of the touch panel where the user's input is detected is higher than a preset threshold, the biometric information is obtained through the biometric sensor using the first light source. The method may include the operation of identifying the capacitance of at least one point of the touch panel where the user's input is detected and the operation of comparing the capacitance of the at least one point with the preset threshold. The method may include the operation of generating a third image by combining a first image obtained using the first light source and a second image obtained using the second light source and the operation of obtaining the biometric information using the third image. The context information may include a security level corresponding to the electronic device. The method may include the operation of obtaining the biometric information based on the first light source when the security level is higher than a predesignated security level. The method may include the operation of performing spoofing filtering using at least one of the first light source and the touch panel and the operation of identifying the context information according to a result of the spoofing filtering. The detailed description of the method is the same as that of the electronic device and is thus omitted.

The embodiments disclosed herein are proposed for description and understanding of the disclosed technology and does not limit the scope of the disclosure. Accordingly, the scope of the disclosure should be interpreted as including all changes or various embodiments based on the technical spirit of the disclosure.

The invention claimed is:

1. An electronic device, comprising:
a biometric sensor configured to obtain fingerprint information related to a user;
a light emitting circuit including a first light source configured to output infrared light;
a display panel including one or more pixels which includes a second light source configured to output visible light; and
a processor configured to:
identify context information including information on a wet or dry state of the user's finger,
select at least one light source from the first light source and the second light source based on the context information including the information on the wet or dry state of the user's finger, and
obtain fingerprint information through the biometric sensor using the selected at least one light source.

2. The electronic device of claim 1, wherein the context information includes information about whether the first light source is additionally needed to obtain fingerprint information based on a state of an image obtained using the biometric sensor.

3. The electronic device of claim 2, wherein when the first light source is determined to be additionally needed, the processor is configured to obtain additional fingerprint information through the biometric sensor using the infrared light output from the first light source.

4. The electronic device of claim 1, further comprising a touch panel disposed on the display panel, wherein the context information includes a capacitance of the touch panel according to the user's input to the touch panel detected to obtain the user's fingerprint information, and wherein the processor is configured to obtain the fingerprint information through the biometric sensor using the infrared light output from the first light source when the capacitance of the touch panel where the user's input is detected is higher than a preset threshold.

5. The electronic device of claim 4, wherein the processor is configured to identify a capacitance for at least one point of the touch panel where the user's input is detected and compare the identified capacitance for the at least one point with the preset threshold.

6. The electronic device of claim 1, wherein the processor is configured to generate a third image by combining a first image obtained using the infrared light output from the first light source and a second image obtained using the visible light output from the second light source and obtain the fingerprint information using the generated third image.

7. The electronic device of claim 1, wherein the context information includes a security level corresponding to the electronic device, and wherein the processor is configured to obtain the fingerprint information based on the infrared light output from the first light source when the security level is higher than a predesignated security level.

8. The electronic device of claim 1, wherein the processor is configured to perform spoofing filtering using capacitances of the touch panel and identify the context information according to a result of the spoofing filtering.

9. A non-transitory computer-readable recording medium retaining a program executed on a computer, wherein the program comprises executable instructions that, when executed by a processor, enable the processor to:
   identify context information including information on a wet or dry state of a user's finger,
   select at least one light source from a first light source configured to output infrared light and a second light source which is included in one or more pixels of a display panel and is configured to output visible light, based on the context information including the information on the wet or dry state of the user's finger, and
   obtain fingerprint information through a biometric sensor to obtain fingerprint information related to the user using the selected at least one light source.

10. The non-transitory recording medium of claim 9, wherein the context information includes information about whether the first light source is additionally needed to obtain the fingerprint information based on a state of an image obtained using the biometric sensor.

11. The non-transitory recording medium of claim 10, wherein when the processor determines that the first light source is additionally needed, the processor is enabled to obtain additional fingerprint information through the biometric sensor using the infrared light output from the first light source.

12. The non-transitory recording medium of claim 9, wherein the context information includes a capacitance of a touch panel disposed on the display which is detected to obtain the user's fingerprint information, and wherein the processor is enabled to obtain the fingerprint information through the biometric sensor using the infrared light output from the first light source when the capacitance of the touch panel where the user's input is detected is higher than a preset threshold.

13. The non-transitory recording medium of claim 12, wherein the processor is enabled to identify a capacitance for at least one point of the touch panel where the user's input is detected and compare the capacitance for the at least one point with the preset threshold.

14. The non-transitory recording medium of claim 9, wherein the processor is enabled to generate a third image by combining a first image obtained using the infrared light output from the first light source and a second image obtained using the visible light output from the second light source and obtain the fingerprint information using the third image.

15. The non-transitory recording medium of claim 9, wherein the context information includes a security level corresponding to the electronic device, and wherein the processor is enabled to obtain the fingerprint information based on the infrared light output from the first light source when the security level is higher than a predesignated security level.

* * * * *